(12) United States Patent
Sharma et al.

(10) Patent No.: US 11,944,423 B2
(45) Date of Patent: Apr. 2, 2024

(54) IN-VIVO MONITORING OF AN INTERNAL VOLUME OF A MAMMAL USING MAGNETIC FIELD GRADIENTS

(71) Applicant: California Institute of Technology, Pasadena, CA (US)

(72) Inventors: Saransh Sharma, Pasadena, CA (US); Mikhail Shapiro, Los Angeles, CA (US); Azita Emami, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 243 days.

(21) Appl. No.: 17/097,421

(22) Filed: Nov. 13, 2020

(65) Prior Publication Data

US 2021/0137412 A1  May 13, 2021

Related U.S. Application Data

(60) Provisional application No. 62/934,763, filed on Nov. 13, 2019, provisional application No. 62/934,767, filed on Nov. 13, 2019.

(51) Int. Cl.
*A61B 5/07* (2006.01)
*A61B 5/00* (2006.01)
(Continued)

(52) U.S. Cl.
CPC .............. *A61B 5/073* (2013.01); *A61B 5/05* (2013.01); *A61B 5/076* (2013.01); *A61B 5/6861* (2013.01);
(Continued)

(58) Field of Classification Search
None
See application file for complete search history.

(56) References Cited

U.S. PATENT DOCUMENTS 9,915,641 B2  3/2018  Shapiro et al.
10,466,277 B1  11/2019  Brooks
(Continued)

FOREIGN PATENT DOCUMENTS

JP  10199724 A  7/1998
JP  2014166306 A  *  9/2014
JP  2014166306 A  9/2014

OTHER PUBLICATIONS

Machine English translation of JP-2014166306-A, Clarivate Analytics, 13 pages, printed on Oct. 26, 2022 (Year: 2022).*
(Continued)

*Primary Examiner* — Devin B Henson
*Assistant Examiner* — Matthew Eric Ogles
(74) *Attorney, Agent, or Firm* — Intrinsic Law Corp.

(57) ABSTRACT

A method for in-vivo monitoring of a target internal volume of a mammal that includes: (a) placing the target internal volume proximal to a three-dimensional magnetic field generator; (b) generating first, second, and third magnetic field gradients along respective first, second, and third axes that are mutually orthogonal; (c) measuring first, second, and third magnetic fields with a three-dimensional magnetic sensor disposed in an ingestible capsule, the ingestible capsule disposed in the target internal volume; (d) with a controller in electrical communication with the three-dimensional magnetic sensor, generating a magnetic sensor output signal that encodes a measurement of the first, second, and third magnetic fields; (e) broadcasting the magnetic sensor output signal from an antenna disposed in the ingestible capsule, and (f) receiving the magnetic sensor output signal with a receiver. The received magnetic field data can be used to determine the three-dimensional position of the ingestible capsule.

20 Claims, 17 Drawing Sheets

(51) Int. Cl.
  A61B 5/05    (2021.01)
  G01B 7/31    (2006.01)
  G01R 33/022  (2006.01)
  G01R 33/385  (2006.01)
(52) U.S. Cl.
  CPC ............ *G01B 7/31* (2013.01); *G01R 33/022* (2013.01); *G01R 33/385* (2013.01); *A61B 2562/0223* (2013.01)

(56) References Cited

U.S. PATENT DOCUMENTS

| | | | | |
|---|---|---|---|---|
| 2011/0009697 | A1* | 1/2011 | Kawano | A61B 1/041 600/117 |
| 2013/0303878 | A1 | 11/2013 | Nevo et al. | |
| 2014/0167762 | A1* | 6/2014 | Sugiyama | G01R 33/3858 324/322 |
| 2015/0297065 | A1 | 10/2015 | Park et al. | |
| 2016/0022123 | A1* | 1/2016 | Katznelson | H01F 7/204 600/118 |
| 2019/0388105 | A1 | 12/2019 | Sharma et al. | |

OTHER PUBLICATIONS

Machine English Translation of Sato, JP-2014166306-A, 2014, pp. 1-13, Printed on Oct. 26, 2022 (Year: 2014).*
Machine English Translation of Sato JP-2014166306-A, 2014, pp. 1-13, Printed Oct. 26, 2022 (Year: 2014).*
W. M. Ricci et al., "Intramedullary Nailing of Femoral Shaft Fractures: Current Concepts," JAAOS, 2009, pp. 296-305, vol. 17, No. 5.
A. Wang et al., "Wireless Capsule Endoscopy," Technology Status Evalutation Reports, 2013, pp. 805-815, vol. 78, No. 6, Elsevier.
U. Mezger et al., "Navigation in surgery," Langenbeck's Archives of Surgery, 2013, pp. 501-514, vol. 398, No. 4, Springer.
H. M. Kremers et al., "Prevalence of Total Hip and Knee Replacement in the United States," The Journal of bone and joint surgery. American volume, 2015, pp. 1386-1397, vol. 97, No. 17, The Journal of Bone and Joint Surgery, Incorporated.
D. Vasisht et al., "In-body backscatter communication and localization," Proceedings of the 2018 Conference of the ACM Special Interest Group on Data Communication (SIGCOMM '18). Association for Computing Machinery, Aug. 2018, pp. 132-146, New York, NY, USA.
A. L. Simpson et al., "Comparison Study of Intraoperative Surface Acquisition Methods for Surgical Navigation," IEEE Transactions on Biomedical Engineering, 2013, pp. 1090-1099, vol. 60, No. 4, IEEE.
D. Formica et al., "Biological effects of exposure to magnetic resonance imaging: an overview," BioMedical Eng. OnLine, 2004, pp. 1-12, vol. 3, No. 11, BioMed Central Ltd.

V. Grover et al., "Magnetic Resonance Imaging: Principles and Techniques: Lessons for Clinicians," Journal of Clinical and Experimental Hepatology, 2015, pp. 246-255, vol. 5, No. 3, Elsevier Inc.
M. Monge et al., "Localization of microscale devices in vivo using addressable transmitters operated as magnetic spins," Nature Biomedical Engineering, 2017, vol. 6, pp. 736-744, Springer Nature Limited.
J. Marques et al., "Low-Field MRI: An MR Physics Perspective," Journal of Magnetic Resonance Imaging, 2019, pp. 1528-1542, vol. 49, No. 6, Wiley Online Library.
D. Son et al., "A 5-D Localization Method for a Magnetically Manipulated Untethered Robot using a 2-D Array of Hall-effect Sensors," IEEE/ASME Transactions on Mechatronics, 2016, pp. 708-716, vol. 21, No. 2, IEEE.
A. Emami et al., "MRI-Inspired High-Resolution Localization for Biomedical Applications: Artificial Nuclear Spins on a Chip," IEEE Solid-State Circuits Magazine, 2018, pp. 34-42, vol. 10, No. 4, IEEE.
Rao et al., "Evaluation of gastrointestinal transit in clinical practice: position paper of the American and European Neurogastroenterology and Motility Societies", Neurogastroenterology & Motility, 2011, vol. 23, 8-23, Blackwell Publishing Ltd.
Hoffman et al., "Gastrointestinal Motility Monitor (GIMM)," Journal of Visualized Experiments, 2010, pp. 1-3, vol. 1, No. 46, JOVE.
Keller et al., "Advances in the diagnosis and classification of gastric and intestinal motility disorders," Nature Reviews, Gastroenterology & Hepatology, 2018, pp. 291-308, vol. 15, Springer Nature Limited.
Medtronic, "SmartPill Motility Testing System", Motility Testing, https://www.medtronic.com/covidien/en-us/products/motility-testing/smartpill-motility-testing-system.html#/smartpill-motility-capsule.
Lo et al., "A Wireless Implant for Gastrointestinal Motility Disorders," Micromachines, 2018, pp. 1-13, vol. 9, No. 17, MDPI.
T. Leloup et al., "A Novel Technique for Distal Locking of Intramedullary Nail Based on Two Non-constrained Fluoroscopic Images and Navigation," IEEE Trans. Med. Imaging, 2008, pp. 1202-1212, vol. 27, No. 9, IEEE.
A. M. Franz et al., "Electromagnetic Tracking in Medicine—A Review of Technology, Validation, and Applications," IEEE Trans. Med. Imaging, Aug. 2014, pp. 1702-1725, vol. 33, No. 8, IEEE.
F. Chen et al., "3D Catheter Shape Determination for Endovascular Navigation Using a Two-Step Particle Filter and Ultrasound Scanning," IEEE Trans. Med. Imaging, 2017, pp. 685-695, vol. 36, No. 3, IEEE.
F. Parent et al., "Intra-Arterial Image Guidance With Optical Frequency Domain Reflectometry Shape Sensing," IEEE Trans. Med. Imaging, 2019, pp. 482-492, vol. 38, No. 2, IEEE.
M. M. Ahmadi et al., "A Wireless-Implantable Microsystem for Continuous Blood Glucose Monitoring," IEEE Transactions on Biomedical Circuits and Systems, 2009, pp. 169-180, vol. 3, No. 3, IEEE.
ISA, "International Search Report", PCT/US20/60433, dated Mar. 9, 2021.
ISA, "International Search Report", PCT/US20/60420, dated Mar. 9, 2021.

* cited by examiner

IN-VIVO MONITORING OF AN INTERNAL VOLUME OF A MAMMAL USING MAGNETIC FIELD GRADIENTS

CROSS-REFERENCE TO RELATED APPLICATIONS

This application claims priority to U.S. Provisional Application No. 62/934,763, titled "Real-Time GI Tract Monitoring with High Precision in 3D Using ATOMS Microchips," filed on Nov. 13, 2019 and to U.S. Provisional Application No. 62/934,767, titled "Magnetic Gradient Coil Design For Micro-Device Localization," filed on Nov. 13, 2019, which are hereby incorporated by reference.

STATEMENT REGARDING FEDERALLY-SPONSORED RESEARCH

This invention was made with government support under Grant No. CBET1823036 awarded by the National Science Foundation. The government has certain rights in the invention.

TECHNICAL FIELD

This application relates generally to medical devices for monitoring an internal volume of a subject using magnetic sensors.

BACKGROUND

Gastrointestinal (GI) transit and motility disorders are increasingly common and cause either delayed or accelerated transit through various regions of the GI tract. These affect one-third of the population and expend significant health care resources. Continuous monitoring and transit time evaluation of the GI tract can provide valuable diagnostic information for patients suffering from chronic constipation, gastroparesis and irritable bowel movement.

Substantial advances have been made to help diagnose GI motility disorders using anorectal manometry, reflux testing, breath testing, radio-opaque markers, scintigraphy and wireless motility capsules. Breath testing is limited by accuracy and quantitative results for gastric emptying (GE) while radio-opaque markers and scintigraphy require exposure to radiation for measuring GE time. Owing to their ease of use and not requiring clinical visits, wireless motility capsules have gained popularity over the past decade. The SmartPill by Medtronic is an example of such a wireless capsule, which helps in localizing transit abnormalities to specific GI regions. As the SmartPill travels through the GI tract, it measures the transit time, pH, pressure and temperature but lacks the capability of real-time position tracking. The receiver for SmartPill is worn by the patient on the waist for 3-5 days, causing inconvenience during daily activities. Another wireless device to modulate and monitor GI motility includes an electrode array that can electrically stimulate and record motility at the implant site. However, a midline abdominal incision is required to implant this device, thus necessitating surgical intervention.

It would be desirable to overcome these and/or other deficiencies in the art.

SUMMARY

The present disclosure and invention can be applied to subjects including living mammals and including humans. Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a method for in-vivo monitoring of a target internal volume of a mammal, comprising: placing the target internal volume proximal to a three-dimensional magnetic field generator; using the three-dimensional magnetic field generator to sequentially produce: a first localization magnetic field gradient along a first axis, at least a portion of the first localization magnetic field gradient having a monotonically-varying magnetic field magnitude along the first axis, the first localization magnetic field gradient produced at a first time; a second localization magnetic field gradient along a second axis that is orthogonal to the first axis, at least a portion of the second localization magnetic field gradient having a monotonically-varying magnetic field magnitude along the second axis, the second localization magnetic field gradient produced at a second time that is different than the first time; and a third localization magnetic field gradient along a third axis that is orthogonal to the first and second axes, at least a portion of the third localization magnetic field gradient having a monotonically-varying magnetic field magnitude along the third axis, the third localization magnetic field gradient produced at a third time that is different than the first and second time; measuring a total magnetic field magnitude at the first, second, and third times; a three-dimensional magnetic sensor disposed in an ingestible capsule, the ingestible capsule disposed in the target internal volume; with a controller in electrical communication with the three-dimensional magnetic sensor, generating a magnetic sensor output signal that encodes a first total magnetic field magnitude measurement, a second total magnetic field magnitude measurement, and a third total magnetic field magnitude measurement that correspond to the first, second, and third magnetic field gradients, respectively; broadcasting the magnetic sensor output signal from an antenna disposed in the ingestible capsule, the antenna electrically coupled to the controller; and receiving the magnetic sensor output signal with a receiver.

In one or more embodiments, the method further comprises ingesting the ingestible capsule. In one or more embodiments, the method further comprises simultaneously producing: a first magnetic field gradient along the first axis with a first planar electromagnet coil set, and a third magnetic field gradient along the third axis with a third planar electromagnet coil set, wherein the first localization magnetic field gradient comprises a first total magnetic field of the first magnetic field gradient and the third magnetic field gradient. In one or more embodiments, the method further comprises measuring a first total magnetic field magnitude of the first total magnetic field with the three-dimensional magnetic sensor while only the first and third magnetic field gradients are simultaneously generated.

In one or more embodiments, the method further comprises after measuring the first magnetic field gradient, simultaneously: turning off the first magnetic field gradient; turning on a second magnetic field gradient along the second axis with a second planar electromagnet coil set; and simultaneously generating only the second and the third magnetic field gradients, wherein the second localization magnetic field gradient comprises a second total magnetic field of the second magnetic field gradient and the third magnetic field gradient.

In one or more embodiments, the method further comprises measuring a second total magnetic field magnitude of the second total magnetic field with the three-dimensional magnetic sensor while only the second and third magnetic field gradients are simultaneously generated. In one or more embodiments, the method further comprises after measuring the second magnetic field gradient: turning off the second magnetic field gradient while continuing to produce the third magnetic field gradient, wherein the third localization magnetic field gradient comprises a third total magnetic field of the third magnetic field gradient; and measuring a third total magnetic field magnitude of the third total magnetic field while only the third magnetic field gradient is turned on.

In one or more embodiments, the method further comprises sending a control signal from the receiver to a controller that causes the three-dimensional magnetic sensor to sequentially measure the total magnetic field magnitude at the first, second, and third times. In one or more embodiments, the method further comprises determining a three-dimensional spatial location of the ingestible capsule based on the first total magnetic field magnitude measurement, the second total magnetic field magnitude measurement, and the third total magnetic field magnitude measurement, the spatial location determined relative to the three-dimensional magnetic field generator. In one or more embodiments, the method further comprises using a look-up table to determine the spatial location, the look-up table including a plurality of reference total magnetic field measurements taken at known locations relative to the three-dimensional magnetic field generator.

Another aspect of the invention is directed to a system for in-vivo monitoring of an internal volume of a mammal, comprising: a three-dimensional magnetic field generator configured to sequentially produce: a first localization magnetic field gradient along a first axis, at least a portion of the first localization magnetic field gradient having a monotonically-varying magnetic field magnitude along the first axis, a second localization magnetic field gradient along a second axis that is orthogonal to the first axis, at least a portion of the second localization magnetic field gradient having a monotonically-varying magnetic field magnitude along the second axis, and a third localization magnetic field gradient along a third axis that is orthogonal to the first and second axes, at least a portion of the third localization magnetic field gradient having a monotonically-varying magnetic field magnitude along the third axis; and an ingestible magnetic sensor comprising: a three-dimensional magnetic sensor that outputs a measurement of a first, a second, and a third magnetic field corresponding to the first, second, and third localization magnetic field gradients, respectively; a controller electrically coupled to the three-dimensional magnetic sensor, the controller generating a magnetic sensor output signal that encodes the measurement of the first, second, and third magnetic fields; an antenna electrically coupled to the controller, the antenna broadcasting the magnetic sensor output signal; a power source electrically coupled to the three-dimensional magnetic sensor and the controller; and an ingestible capsule having an internal cavity in which the three-dimensional magnetic sensor, the controller, the antenna, and the power source are disposed.

In one or more embodiments, the three-dimensional magnetic field generator comprises: a first magnetic field gradient coil configured to generate a first magnetic field gradient along the first axis; a second magnetic field gradient coil configured to generate a second magnetic field gradient along the second axis; a third magnetic field gradient coil configured to generate a third magnetic field gradient along the third axis; and a controller configured to selectively provide power to the first electromagnet coil set, the second electromagnet coil set, and/or the third electromagnet coil to sequentially produce the first, second, and third localization magnetic field gradients.

In one or more embodiments, the system further comprises a receiver that receives the magnetic sensor output signal. In one or more embodiments, the receiver is configured to determine a three-dimensional spatial location of the ingestible magnetic sensor based on the measurement of the first, second, and third magnetic fields, the three-dimensional spatial location determined relative to the three-dimensional magnetic field generator. In one or more embodiments, the receiver is configured to display the spatial location on a user interface on or coupled to the receiver.

In one or more embodiments, the controller selectively provides power to only the first and third magnetic field gradient coils to simultaneously generate only the first and third magnetic field gradients, wherein the first localization magnetic field gradient comprises a total magnetic field of the first and third magnetic field gradients, and the three-dimensional magnetic sensor measures the first magnetic field while only the first and third magnetic field gradients are generated.

In one or more embodiments, the controller selectively provides power to only the second and third magnetic field gradient coils to simultaneously generate only the second and third magnetic field gradients, wherein the second localization magnetic field gradient comprises a total magnetic field of the second and third magnetic field gradients, and the three-dimensional magnetic sensor measures the second magnetic field while only the second and third magnetic field gradients are generated.

In one or more embodiments, the controller selectively provides power to only the third magnetic field gradient coil to generate only the third magnetic field gradient, wherein the third localization magnetic field gradient comprises a total magnetic field of the third magnetic field gradients, and the three-dimensional magnetic sensor measures the third magnetic field while only the third magnetic field gradient is generated.

In one or more embodiments, the ingestible magnetic sensor further comprises an antenna-matching circuit disposed between the controller and the antenna. In one or more embodiments, the three-dimensional magnetic field generator is disposed on a back of a chair or on a platform.

In one or more embodiments, the first magnetic field gradient coil set has a width that is parallel to the first axis, and a ratio of (a) the at least a portion of the first localization magnetic field gradient that has the monotonically-varying magnetic field magnitude along the first axis to (b) the width of the first planar electromagnet coil set is within a range of about 1:2 to about 3:4. In one or more embodiments, the second planar electromagnet coil set has a length that is parallel to the second axis, and a ratio of (c) the at least a portion of the second localization magnetic field gradient that has the monotonically-varying magnetic field magnitude along the second axis to (d) the length of the second planar electromagnet coil set is within a range of about 1:2 to about 3:4. In one or more embodiments, the third planar electromagnet coil set has a shape of an annulus having an inner diameter and an outer diameter, and a ratio of (e) the at least a portion of the third localization magnetic field gradient that has the monotonically-varying magnetic field magnitude along the third axis to (f) the outer diameter of the annulus is within a range of about 1:4 to about 2:5.

BRIEF DESCRIPTION OF THE DRAWINGS

For a fuller understanding of the nature and advantages of the present concepts, reference is made to the detailed description of preferred embodiments and the accompanying drawings.

DETAILED DESCRIPTION

Figure 1:
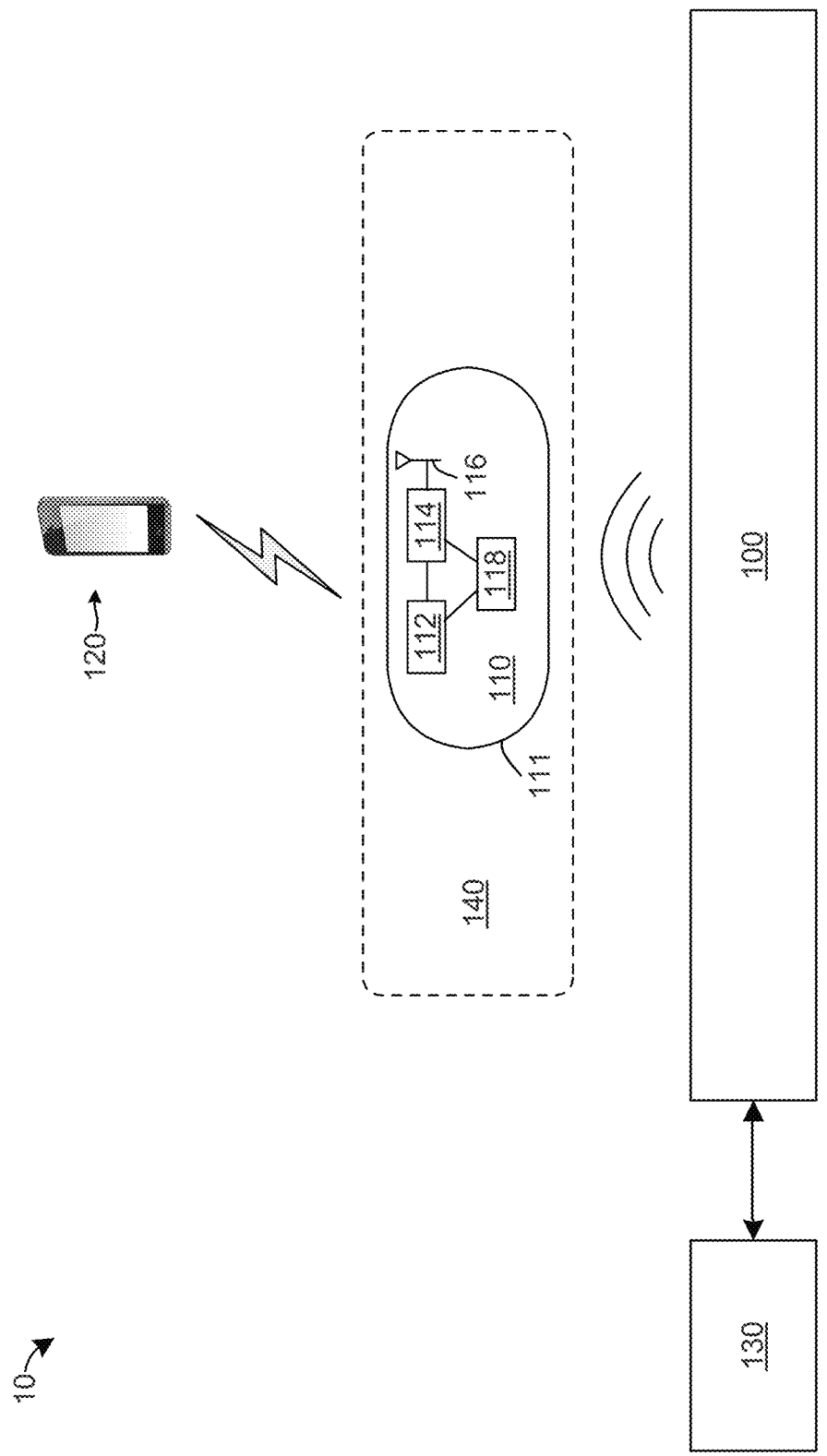
FIG. 1 is a block diagram of a system for in-vivo monitoring of an internal volume of a mammal.

A non-invasive internal monitoring system for a subject (e.g., a mammal, including a human) can localize microscale devices in the GI tract (or other internal volume or cavity in the mammal) with sub-mm spatial resolution in real-time. A monotonically-varying magnetic field gradient is produced along each of three orthogonal axes (e.g., in the Cartesian X, Y, and Z axes) in a desired field-of-view (FOV), which is sensed by an ingestible magnetic sensor moving through the GI tract. The measured three-dimensional magnetic field value by the ingestible magnetic sensor is transmitted wirelessly to an external receiver (e.g., a smartphone), which can determine the corresponding spatial location. Owing to the monotonic nature of the magnetic field gradients in the FOV, each spatial point is encoded uniquely, thus allowing unambiguous position mapping from the field values. The ingestible magnetic sensor device can also measure and report pH, temperature, pressure, and other biologically-useful markers, along with their real-time location, thus providing a spatiotemporal map for more comprehensive patient diagnosis. For example, the ingestible magnetic sensor device can be coupled to on-chip and/or off-chip sensors that measure pH, temperature, pressure, and other biologically-useful markers. Data corresponding to these values can be transmitted during wireless reporting of the measured magnetic field.

The GI tract monitoring system includes of a three-dimensional magnetic field generator (e.g., electromagnetic coils) for generating the desired magnetic field gradient, an ingestible magnetic sensor for sensing the three-dimensional magnetic field at the location ingestible magnetic sensor, and an external receiver for mapping the three-dimensional magnetic field values to distinct points in space. The ingestible magnetic sensor can be ingested as a capsule by the patient and the three-dimensional magnetic field generator is placed near the patient, for example behind the subject's back, similar to a wall, or on the back of a chair in the case of human subjects. Those skilled in the art will understand how to generalize the present disclosure to other non-human subjects as suitable for a given application. An external receiver, for example a smartphone, communicates wirelessly with the ingestible magnetic sensor moving in the GI tract to trigger a magnetic field measurement and receive the raw field data. A user interface on the external device then displays the real-time position of the ingestible magnetic sensor with respect to the three-dimensional magnetic field generator's location.

For a given magnetic field resolution that the ingestible magnetic sensor can measure ($\Delta B$), the gradient strength (G) of the magnetic field gradient is determined by the required localization resolution ($\Delta X$), as given by the relation $\Delta X = \Delta B / G$. In one embodiment, $\Delta B$ is 15 µT and in order to get 500 µm resolution for $\Delta X$, the required G is 30 mT/m. When 25 or more samples of the magnetic field are measured and averaged, the measurement error of the ingestible magnetic sensor can lower from $\Delta B$ of 15 µT to 3 µT, which can improve the spatial resolution from 500 µm to 100 µm for a given magnetic field gradient strength of 30 mT/m.

Throughout this disclosure, specific examples, preferred embodiments, and illustrations are provided to explain exemplary aspects and embodiments of the invention. These are not intended to be limiting, and rather, those skilled in the art will understand that many other examples and embodiments may be developed and implemented as suits a given application of the present systems and methods. All of these variations are comprehended by this disclosure and appended claims.

FIG. 1 is a block diagram of a system 10 for in-vivo monitoring of an internal volume of a mammal according to an embodiment. The system 10 includes a three-dimensional magnetic field generator 100, an ingestible magnetic sensor 110, and a receiver 120. The three-dimensional magnetic field generator 100 is configured to generate magnetic field gradients along or parallel to multiple mutually-orthogonal axes. For example, the three-dimensional magnetic field generator 100 can generate a first localization magnetic field gradient along or parallel to a first axis, a second localization magnetic field gradient along or parallel to a second axis, and a third localization magnetic field gradient along or parallel to a third axis. The first, second, and third axis are orthogonal to one another. In the Cartesian coordinate system, the first axis can correspond to the "X" axis, the second axis can correspond to the "Y" axis, and the third axis can correspond to the "Z" axis. At least a portion and/or at least a substantial portion of each magnetic field gradient can have a monotonically-varying magnitude along the respective axis. In some embodiments, each localization magnetic field gradient magnitude can vary linearly or non-linearly over some or all of the respective magnetic field gradient.

The three-dimensional magnetic field generator 100 can have example dimensions of about 60 cm in length (e.g., parallel to the "X" direction), about 60 cm in width (e.g., parallel to the "y" direction), and about 2 cm in about 60 cm in height (e.g., parallel to the "Z" direction). This can correspond to a monotonic FOV of about 40 cm in length (e.g., parallel to the "X" direction), about 40 cm in width (e.g., parallel to the "y" direction), and about 30 cm in height (e.g., parallel to the "Z" direction). The monotonic FOV can be the dimensions over which the magnetic field gradient has a monotonically-varying magnitude such that each magnetic field measurement corresponds to or encodes a unique relative spatial position.

In some embodiments, the three-dimensional magnetic field generator 100 includes a plurality of coils that are configured to produce the three localization magnetic field gradients. For example, the three-dimensional magnetic field generator 100 can include one or more coils that is/are configured to produce the first localization magnetic field gradient, one or more coils that is/are configured to produce the second localization magnetic field gradient, and one or more coils that is/are configured to produce the third localization magnetic field gradient. Examples of this coil configuration are disclosed in (a) U.S. Pat. No. 9,915,641, titled "Sensing and Actuation Of Biological Function Using Addressable Transmitters Operated As Magnetic Spins," issued on Mar. 13, 2018, (b) U.S. Pat. No. 10,466,227, titled "Sensing and Actuation Of Biological Function Using Addressable Transmitters Operated As Magnetic Spins," issued on Nov. 5, 2019, (c) U.S. Patent Application Publication No. 2019/0388105, titled "Surgical Alignment By Magnetic Field Gradient Localization," published on Dec. 26, 2019, (d) U.S. patent application Ser. No. 17/097,349, titled "Electromagnet Gradient Coil Apparatus For Micro-Device Localization," filed on Nov. 13, 2020, which claims priority to U.S. Provisional Application No. 62/934,763, titled "Real-Time GI Tract Monitoring with High Precision in 3D Using ATOMS Microchips," filed on Nov. 13, 2019, and to Provisional Application No. 62/934,767, titled "Magnetic Gradient Coil Design For Micro-Device Localization," filed on Nov. 13, 2019, and (e) U.S. Provisional Application No. 63/075,980, titled "Precision Surgery Using Smart Surgical Tags," filed on Sep. 9, 2020, which are hereby incorporated by reference.

The three-dimensional magnetic field generator 100 can be controlled using control signals sent from a controller 130. The control signals can identify the magnetic field gradient to produce and its magnitude. The controller 130 can also vary the timing of the control signals such that the magnetic field gradients are produced during a predetermined time sequence, which can encode the magnetic field gradient produced. The control signals can also include the length of time that each magnetic field gradient is turned on. Alternatively, a first control signal can instruct the three-dimensional magnetic field generator 100 to start producing a given magnetic field gradient and a second control signal can instruct the three-dimensional magnetic field generator 100 to stop producing that magnetic field gradient. In some embodiments, the controller and the three-dimensional magnetic field generator 100 are integrated into a single apparatus.

The ingestible magnetic sensor 110 includes an ingestible capsule 111 and a circuit that includes a three-dimensional magnetic sensor 112, a controller 114, an antenna 116, and a power source 118. The ingestible capsule 111 can comprise polydimethylsiloxane (PDMS) or another biosafe material.

The three-dimensional magnetic sensor 112 measures the magnetic field (e.g., total magnetic field) at the position of the ingestible magnetic sensor 110 and outputs the magnetic field measurements to the controller 114. The magnetic field measurements include a measurement of each of the X, Y, and Z field values, which can each be provided as a 16-bit data vector. The three-dimensional magnetic sensor 112 can measure the magnetic field based on control signals received from the controller 114, which can be sent over a protocol such as I2C. In some embodiments, 25 or more measurements of each magnetic field gradient can be taken. The control signals can include a timing sequence for the three-dimensional magnetic sensor 112 to perform the magnetic field measurements. The timing sequence can correspond to the predetermined time sequence of the magnetic field gradients. In addition, the control signals can include configuration settings for power, noise, and frequency of measurement (e.g., 1 to 5 magnetic field measurements per minute) of the three-dimensional magnetic sensor 112. In an example embodiment, the three-dimensional magnetic sensor 112 can comprise an AK09970N Tri-axis Magnetic Sensor IC with Digital Output available from Asahi Kasei Microdevices Corporation, though other three-dimensional magnetic sensors can be used. It is understood that certain examples provided herein are only provided for the purpose of illustration and explanation, and the examples are not limiting of the invention. Those skilled in the art will appreciate substitution of equivalent, similar or other examples without departing from the scope of the disclosure or invention.

The controller 114 includes a microprocessor, local memory (e.g., cache and RAM), and a transceiver that can support one or more wireless protocols such as Bluetooth (e.g., Bluetooth low-energy (LE)), near-field communication (NFC), and/or another wireless protocol. The controller 114 can store the magnetic field measurements in its local memory (e.g., cache or RAM) and then encode the magnetic field measurements in a magnetic sensor output signal. The magnetic sensor output signal is broadcast by the antenna 116 using a wireless protocol (e.g., Bluetooth LE) and sent to the receiver 120. An antenna-matching circuit can be included between the controller 114 and the antenna 116 to improve and/or maximize power transmission to the antenna 116 for radiation. In an example embodiment, the controller 114 can comprise an NRF52832 Bluetooth 5.2 System-on-a-Chip (SoC) available from Nordic Semiconductor, though other microprocessors or SoCs can be used. In addition, the antenna 116 can comprise a 2450AT18B100 2.4 GHz Mini Antenna available from Johanson Technology, Inc.

The power source 118 provides power for the three-dimensional magnetic sensor 112 and the device controller 114. The power source 118 can include a battery such as one or more coin-cell rechargeable batteries (e.g., 3V, 11 mAh) such as the MS920SE available from Seiko Instruments, Inc. In another embodiment, the power source 118 can comprise an inductor that can wirelessly receive energy via inductive coupling. In another embodiment, the power source 118 can derive power biochemically. The power source 118 can receive and/or derive power from other external sources and/or from internal sources.

In some embodiments, the ingestible magnetic sensor 110 can be cylindrical with about a 7.9 mm diameter and about 19 mm in length. Again, the present examples and embodiments are not limiting, and the invention covers many embodiments according to the accompanying claims and as appreciated by those skilled in the art upon review of this disclosure.

The receiver 120 includes a microprocessor and an antenna that can receive the magnetic sensor output signal from the ingestible magnetic sensor 110 using the wireless protocol (e.g., Bluetooth LE). For example, the receiver 120 can comprise a smartphone, a laptop computer, a desktop computer, a tablet, or another computer. The receiver 120 can then map the magnetic field measurements to corresponding spatial coordinates, which can be displayed on an internal display on the receiver 120 and/or on an external display. The corresponding spatial coordinates can be determined using a look-up table, a model, or other relationship stored on the receiver 120. For example, the look-up table can be created by making a series of total magnetic field measurements corresponding to the three localization magnetic field gradients produced by the three-dimensional magnetic field generator 100 at a series of known spatial coordinates proximal to the three-dimensional magnetic field generator 100, such as every 100 µm in each dimension. The Earth's ambient magnetic field can be subtracted from the measured magnetic field measurements in the look-up table.

In addition, the receiver 120 can send control signals and/or commands to the controller 114. The control signals and/or commands (in general, control signals) from the receiver 120 can trigger magnetic field measurements, such as by causing the controller 114 to send control signals to the three-dimensional magnetic sensor 112. The control signals from the receiver 120 can also include a timing sequence for the three-dimensional magnetic sensor 112 to perform the magnetic field measurements. Alternatively, the timing sequence can be created by having the receiver 120 send control signals that trigger magnetic field measurements according to the timing sequence. The control signals from the receiver 120 can also cause the controller 114 to send the magnetic sensor output signal. In addition, the receiver 120 can send control signals to configure the controller 114 and/or the three-dimensional magnetic sensor 112. For example, the receiver 120 can configure the wireless communication settings (e.g., wireless protocol, encryption, etc.) of the controller 114. In addition, the receiver 120 can configure the power, noise, and/or frequency of measurement (e.g., 1 to 5 magnetic field measurements per minute) settings of the three-dimensional magnetic sensor 112.

In operation, the ingestible magnetic sensor 110 is ingested into or placed in the patient. For example, the ingestible magnetic sensor 110 can be ingested into the gastrointestinal (GI) tract 140 of a mammal (e.g., a human patient or other mammal). The three-dimensional magnetic field generator 100 is then placed near the mammal's GI tract 140. For example, the three-dimensional magnetic field generator 100 can be placed on or in a platform (on which the mammal lies down), the back of a chair (in which the mammal sits). Alternatively, the three-dimensional magnetic field generator 100 can be disposed in a wearable device, for example that can be wrapped around the subject's (e.g., mammal's) stomach. The receiver 120 communicates wirelessly with the controller 114 in the ingestible magnetic sensor 110 to trigger a magnetic field measurement and/or receive the raw field data. A user interface on the receiver 120 can display the three-dimensional position of the ingestible magnetic sensor 110 with respect to the position of the three-dimensional magnetic field generator 100.

The receiver 120 can receive and/or display the relative position of the ingestible magnetic sensor 110 in real time (or substantially real time due to transmission times, etc.) or in non-real time (e.g., at a later time). For example, the ingestible magnetic sensor 110 can temporarily store multiple magnetic field measurements and send them as a group to the receiver 120. Additionally or alternatively, the receiver 120 can receive the magnetic field measurements from the ingestible magnetic sensor 110 for display at a later time on the display of the receiver 120 or on another device, such as a computer.

Figure 2:
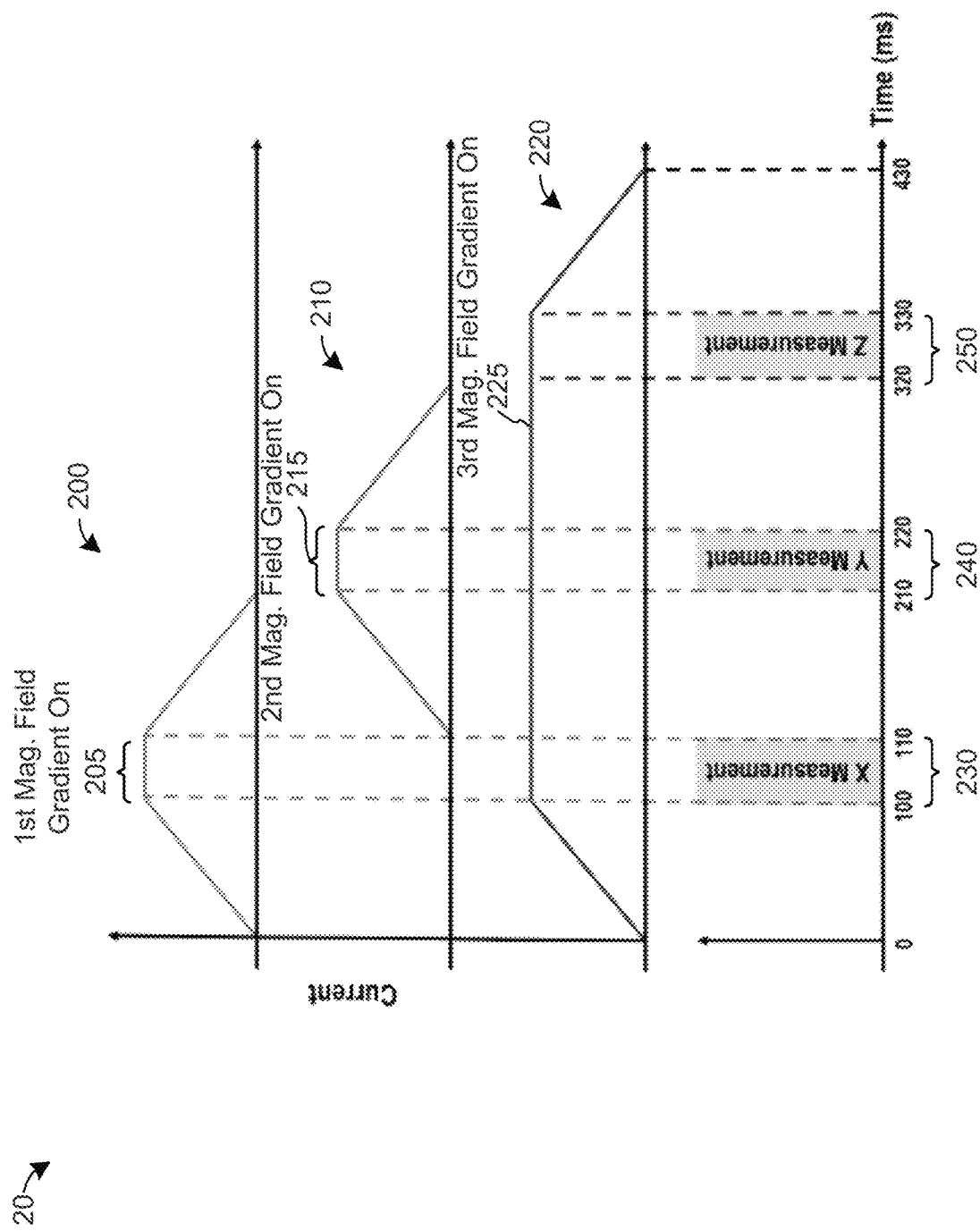
FIG. 2 illustrates an example timing diagram for the three-dimensional magnetic field generator.

FIG. 2 illustrates an example timing diagram 20 for the three-dimensional magnetic field generator 100. The timing diagram 20 includes a first timing diagram 200 that illustrates how the current is ramped up to a plateau which corresponds to the stable "on" time 205 of the first magnetic field gradient (e.g., the X magnetic field gradient). For example, current may flow through one or more coils that are configured to generate the first magnetic field gradient in the first timing diagram 200. The timing diagram 20 also includes a second timing diagram 210 that illustrates how the current is ramped up to a plateau which corresponds to the stable "on" time 215 of the second magnetic field gradient (e.g., the Y magnetic field gradient). For example, current may flow through one or more coils that are configured to generate the second magnetic field gradient in the second timing diagram 210. The timing diagram 20 also includes a third timing diagram 220 that illustrates how the current is ramped up to a plateau which corresponds to the stable "on" time 225 of the third magnetic field gradient (e.g., the Z magnetic field gradient). For example, current may flow through one or more coils that are configured to generate the third magnetic field gradient in the third timing diagram 210.

The timing diagram 20 illustrates that the first and third magnetic field gradients (e.g., the X and Z magnetic field gradients, respectively) are turned on simultaneously at time 0. At 100 ms, both the first and third magnetic field gradients have fully turned on 205, 225. The on time 205 of the first magnetic field gradient corresponds to the first magnetic field measurement window 230 (between 100 and 110 ms) in which the three-dimensional magnetic sensor 112 can measure the magnetic field produced by the first magnetic field gradient. One or more measurements can occur during the first magnetic field measurement window 230. In some embodiments, 25 or more measurements can be taken. Additionally or alternatively, the three-dimensional magnetic sensor 112 can wait a predetermined time period (e.g., 2-5 ms) at the beginning of the first magnetic field measurement window 230 to take the first magnetic field measurement(s) to ensure that the current and the corresponding first magnetic field gradient are stable. The mean or median of multiple first magnetic field measurements can be used as the measured value of the first magnetic field. The third magnetic field gradient remains on 225 during the first magnetic field measurement window 230.

At 110 ms, the three-dimensional magnetic field generator 100 simultaneous turns off (ramps down) the first magnetic field gradient and turns on (ramps up) the second magnetic field gradient. At 210 ms, the second magnetic field gradient (e.g., the Y magnetic field gradient) has fully turned on 215.

The on 215 time of the second magnetic field gradient corresponds to the second magnetic field measurement window 240 (between 210 and 220 ms) in which the three-dimensional magnetic sensor 112 can measure the magnetic field produced by the second magnetic field gradient. One or more measurements can occur during the second magnetic field measurement window 240. In some embodiments, 25 or more measurements can be taken. Additionally or alternatively, the three-dimensional magnetic sensor 112 can wait a predetermined time period (e.g., 2-5 ms) at the beginning of the second magnetic field measurement window 240 to take the second magnetic field measurement(s) to ensure that the current and the corresponding second magnetic field gradient are stable. The mean or median of multiple second magnetic field measurements can be used as the measured value of the second magnetic field. The third magnetic field gradient remains on 225 during the second magnetic field measurement window 240.

At 220 ms, the three-dimensional magnetic field generator 100 turns off (ramps down) the second magnetic field gradient while maintaining the third magnetic field gradient. The third magnetic field measurement window 250 begins at 320 ms when the second magnetic field gradient is fully turned off and lasts until 330 ms. in The three-dimensional magnetic sensor 112 measures the magnetic field produced by the third magnetic field gradient during the third magnetic field measurement window 250. One or more measurements can occur during the third magnetic field measurement window 250. In some embodiments, 25 or more measurements can be taken. Additionally or alternatively, the three-dimensional magnetic sensor 112 can wait a predetermined time period (e.g., 2 to 5 ms) at the beginning of the third magnetic field measurement window 250 to take the third magnetic field measurement(s) to ensure that the current and the corresponding third magnetic field gradient are stable. The mean or median of multiple third magnetic field measurements can be used as the measured value of the third magnetic field.

At the end of the third magnetic field measurement window 250, the three-dimensional magnetic field generator 100 turns off (ramps down) the third magnetic field gradient such that the first, second, and third magnetic field gradients are turned off. In an embodiment, the timing diagram 20 repeats on a periodic basis to take repeated measurements of the three-dimensional magnetic field gradient to determine the corresponding three-dimensional position of the ingestible magnetic sensor 110. For example, the periodic basis of 1-30 minutes, including every 5 minutes, every 10 minutes, every 15 minutes, every 20 minutes, and every 25 minutes. The periodic basis can be more frequent or less frequent than the range of 1-30 minutes. The periodic basis can be selected based on the desired volume of spatial data of the ingestible magnetic sensor 110 as it moves within the mammal and on the capacity of the power source 118, which is used both to power the three-dimensional magnetic sensor 112 and the transmission of data to the receiver 120. It is estimated that a 3V, 11 mAh battery can support a measurement of the three-dimensional magnetic field gradient every minute for 2 weeks. These exemplary figures, durations and values are illustrative, and other examples are fairly understood within the scope of this disclosure and accompanying claims.

It is noted that the third magnetic field gradient remains on 225 during all the measurement windows 230, 240, 250. It was discovered that the absence of the third magnetic field gradient (e.g., the Z magnetic field gradient) causes a parabolic magnetic field profile for the first (X) and second (Y) magnetic field gradients since rotation artifacts of the ingestible magnetic sensor 110 inside the mammal (e.g., inside the gastrointestinal tract) can cause the negative and positive halves to give the same vector field value. This causes the three-dimensional magnetic field generator 100 to have identical magnetic field magnitude profiles in their two halves, which reduces the monotonic FOV to half of the coil size. The third magnetic field gradient adds a background field to both the first and second magnetic field gradient fields, which results in a monotonically-varying magnetic field magnitude for a much bigger coil section, thus enhancing the FOV.

Figure 3:
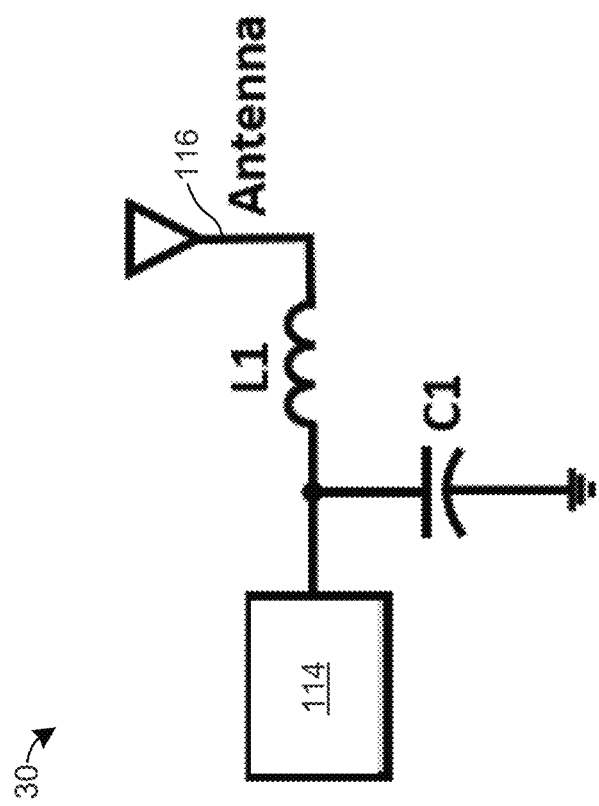
FIG. 3 is a schematic diagram of an antenna-matching circuit antenna-matching circuit.

FIG. 3 is a schematic diagram of an antenna-matching circuit 30 antenna-matching circuit that can be included between the controller 114 and the antenna 116. The antenna matching circuit 30 includes a shunt capacitor C1 followed by a series inductor L1. The shunt capacitor C1 can have a capacitance of about 0.5 to about 2 pF including about 0.75 pF, about 1 pF, about 1.25 pF, about 1.5 pF, and about 1.75 pF. The inductor L1 can have an inductance of about 3 to about 5 nH including about 3.5 nH, about 4 nH, and about 4.5 nH. As used herein, "about" means plus or minus 5% to 10% of the relevant value. The antenna matching circuit 30 is preferably accurately matched to the antenna 116 to minimize power losses from the controller 114 to the antenna 116.

Figure 4:
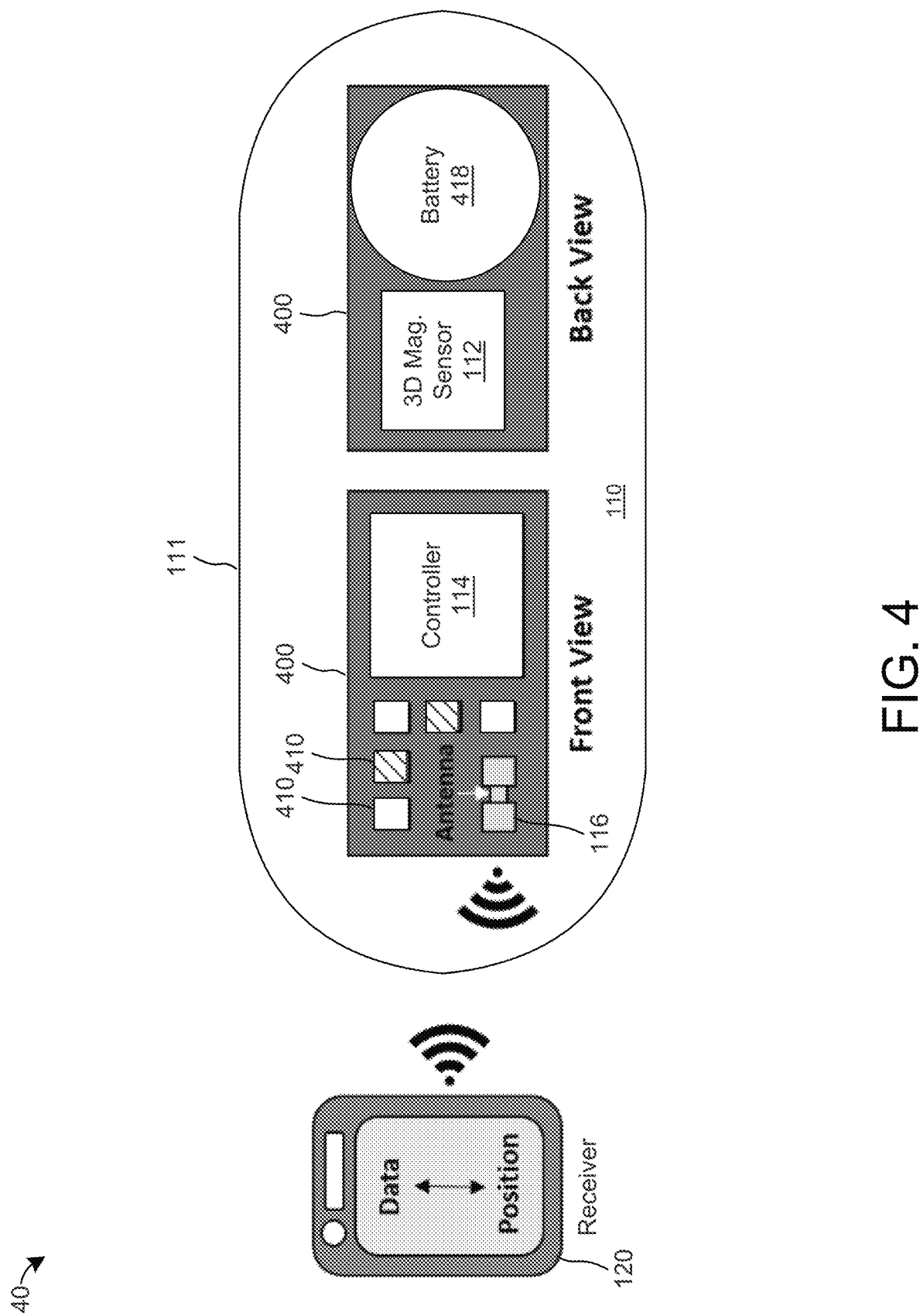
FIG. 4 is a block diagram of a system for in-vivo monitoring of an internal volume of a mammal.

FIG. 4 is a block diagram of a system 40 for in-vivo monitoring of an internal volume of a mammal according to an embodiment. System 40 includes the ingestible magnetic sensor 110 and the receiver 120 of system 10. The three-dimensional magnetic sensor 112, controller 114, antenna 116, and battery 418 are mounted on a substrate 400 such as a printed circuit board (e.g., FR4 substrate). Though FIG. 4 illustrates both the front and back sides of the substrate 400, it is noted that the ingestible magnetic sensor 110 typically only includes one substrate 400. In other words, the front and back sides of the substrate 400 are illustrated for reference in FIG. 4. However, in other embodiments the ingestible magnetic sensor 110 can include more than one substrate 400. The controller 114 and antenna 116 are mounted on the top of the substrate 400, and the three-dimensional magnetic sensor 112 and the battery 418 are mounted on the bottom of the substrate 400. The three-dimensional magnetic sensor 112, controller 114, antenna 116, and battery 418 can be mounted on the substrate 400 in different configurations. In another embodiment, the battery 418 can be replaced with and/or can include the power source 118.

The three-dimensional magnetic sensor 112, controller 114, antenna 116, and battery 418 are electrically connected by lines or wires formed in or on the substrate 400 to form a circuit. In addition, one or more noise-cancellation capacitors 410 (e.g., for the controller 114) and one or more pull-up resistors 420 (e.g., for the three-dimensional magnetic sensor 112) can be mounted on the substrate 400.

Figure 5:
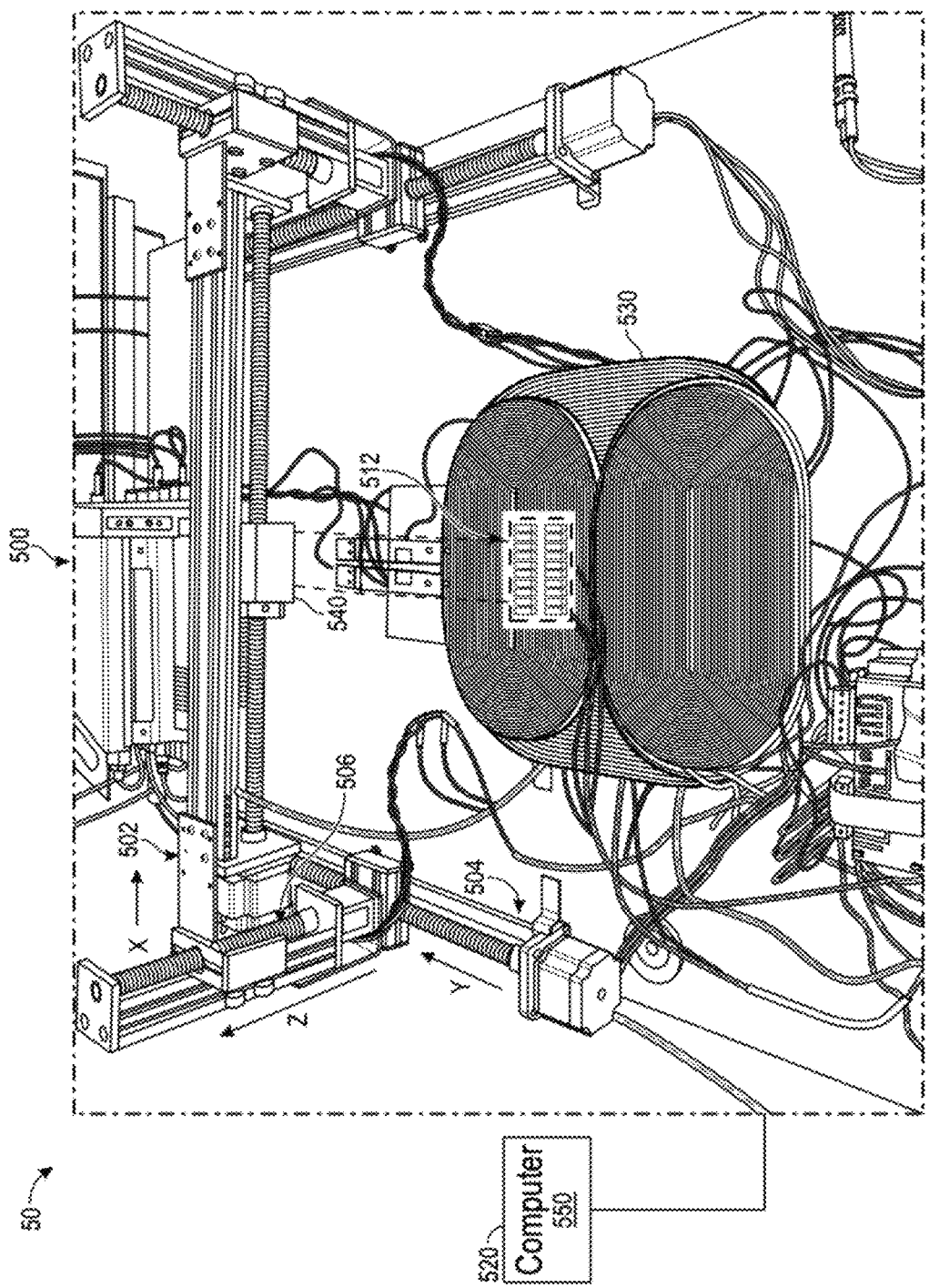
FIG. 5 is an image of an apparatus for mapping the relative spatial coordinates of the magnetic field produced by the three-dimensional magnetic field generator.

FIG. 5 is an image of an apparatus 50 for mapping the relative spatial coordinates of the magnetic field produced by the three-dimensional magnetic field generator 100. The apparatus 50 includes linear actuators 500, a three-dimensional magnetic sensor 512, a controller board 520, and a three-dimensional magnetic field generator 530. The linear actuators 500 include a first linear actuator 502 that can move along a first axis (e.g., the X axis), a second linear actuator 504 that can move along a second axis (e.g., the Y axis) that is orthogonal to the first axis, and a third linear actuator 506 that can move along a third axis (e.g., the Z axis) that is orthogonal to the first and second axes. The linear actuators 500 and the three-dimensional magnetic field generator 530 are controlled by the controller board 520 (e.g., by controller 600 discussed below). The controller board 520 can cause the linear actuators 500 to move stepwise over the entire FOV of the three-dimensional magnetic field generator 530, such as about every 50-250 µm, including about every 100 µm, about every 150 µm, and about every 200 µm. The three-dimensional magnetic sensor 512 is mounted on a fiberglass arm 540 and measures the measures the magnetic field at each location and sends it to the controller 520, which sends it to a computer for creating a look-up table. In some embodiments, multiple measurements are taken at each location and averaged together. For example, 25 or more measurements can be taken at each location.

Figure 6:
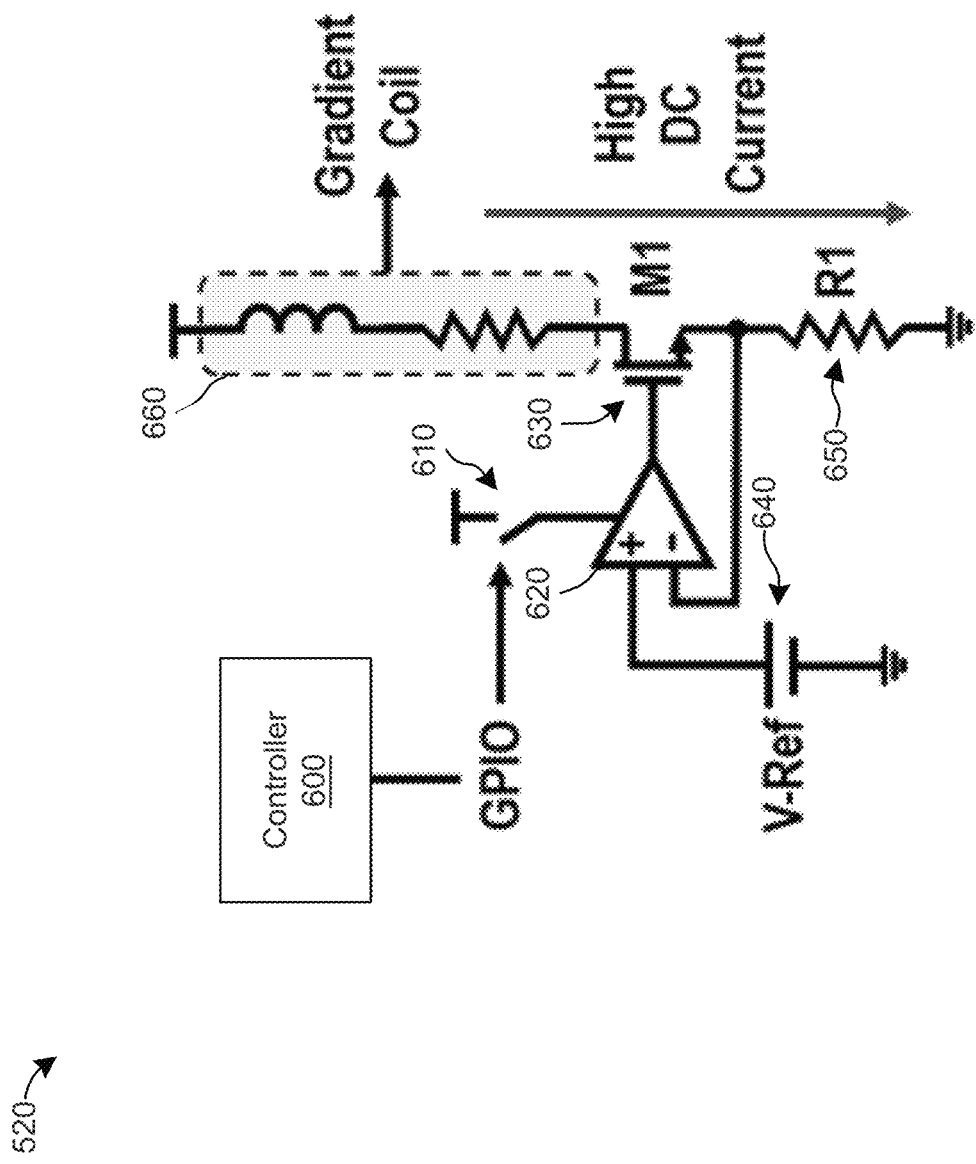
FIG. 6 is a schematic diagram of a controller board.

FIG. 6 is a schematic diagram of the controller board 520. The controller board 520 includes a controller 600, a switch 610, an amplifier 620, a transistor 630, a capacitor 640, and a resistor 650. The controller 600 is electrically coupled to (e.g., over a general-purpose input/output) the switch 610 to control the state of the switch 610 (e.g., open or closed state). The amplifier 620 has inputs that are electrically coupled to the switch 610, the capacitor 640, and the source side of the transistor 630, which can be a MOSFET such as a high-current MOSFET (e.g., PSMN2R7-30PL available from NEXPERIA B.V.). The voltage across the capacitor 640 is a reference voltage VREF. The output of the amplifier 620 is electrically coupled to the gate side of the transistor 630. The resistor 650 is electrically coupled to the source side of the transistor 630. The resistor 650 can be a high-temperature-stability resistor such as the MP930-0.020-5%, available from Caddock Electronics, Inc.

When the switch 610 is closed, current flows through the controller board 520 to provide power to the three-dimensional magnetic field generator 100, such as to one or more magnetic field gradient coils 660 in the three-dimensional magnetic field generator 100. When the switch 610 is open, current does not flow through the controller board 520 and no power is provided to the three-dimensional magnetic field generator 100.

The controller 600 can be configured and/or programmed to have a first setting to produce a first localization magnetic field gradient with respect to the first axis where at least a portion of the first localization magnetic field gradient has a monotonically-varying magnitude (e.g., a first FOV with respect to the first axis) along the first axis. In the first setting, the controller 600 provides power simultaneously only to the first and third electromagnet coil sets. The controller 600 can further be configured and/or programmed to have a second setting to produce a second localization magnetic field gradient with respect to the second axis where at least a portion of the second localization magnetic field gradient has a monotonically-varying magnitude (e.g., a second FOV with respect to the second axis) along the second axis. In the second setting, the controller 600 provides power simultaneously only to the second and third electromagnet coil sets. The controller 600 can further be configured and/or programmed to have a third setting to produce a third localization magnetic field gradient with respect to the third axis where at least a portion of the third localization magnetic field gradient has a monotonically-varying magnitude (e.g., a third FOV with respect to the third axis) along the third axis. In the third setting, the controller 600 provides power simultaneously only to the third electromagnet coil set. The controller 600 can be configured to selective provide power according to the first, second, and third settings sequentially and/or in a predetermined time sequence, both of which can encode the first, second, and third localization magnetic field gradients.

Figure 7:
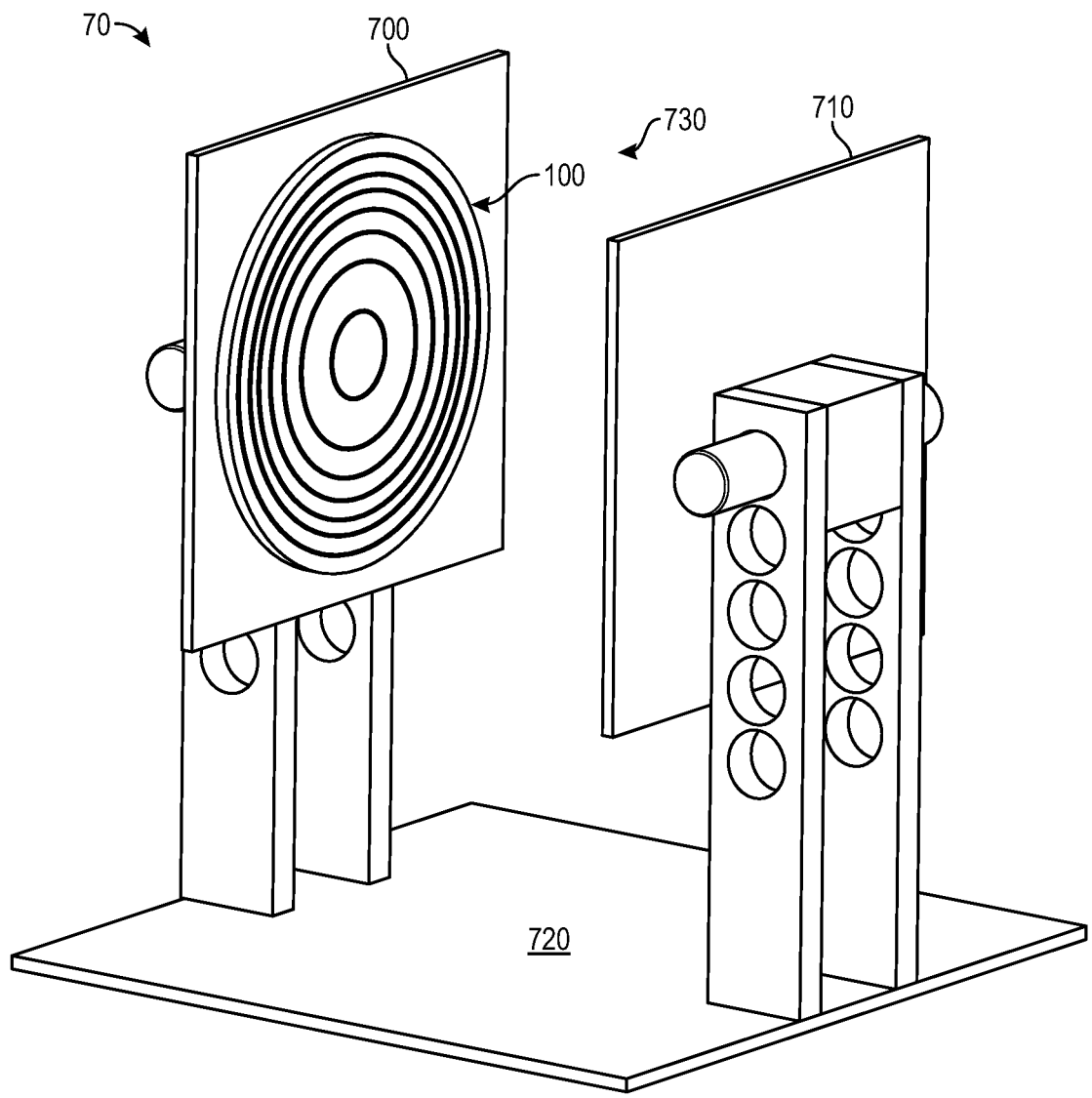
FIG. 7 is a perspective view of an apparatus for mounting a three-dimensional magnetic field generator.

FIG. 7 is a perspective view of an apparatus 70 for mounting a three-dimensional magnetic field generator according to an embodiment. The apparatus 70 includes first and second raised walls 700, 710 that are mounted on a platform 720. The raised walls 700, 710 are spaced apart to form a chute 730 through which a mammal can pass. A three-dimensional magnetic field generator 100 is mounted on one or both raised walls 700, 710. The raised walls 700, 710 are height-adjustable to align the three-dimensional magnetic field generator 100 with the subject or a target volume in the subject (e.g., the mammal/human GI tract). A receiver (e.g., receiver 120) can be used to send a control signal to an ingestible magnetic sensor on or in the mammal to take a magnetic field measurement when the subject passes into the FOV of the three-dimensional magnetic field generator 100 in the chute 730.

Figure 8:
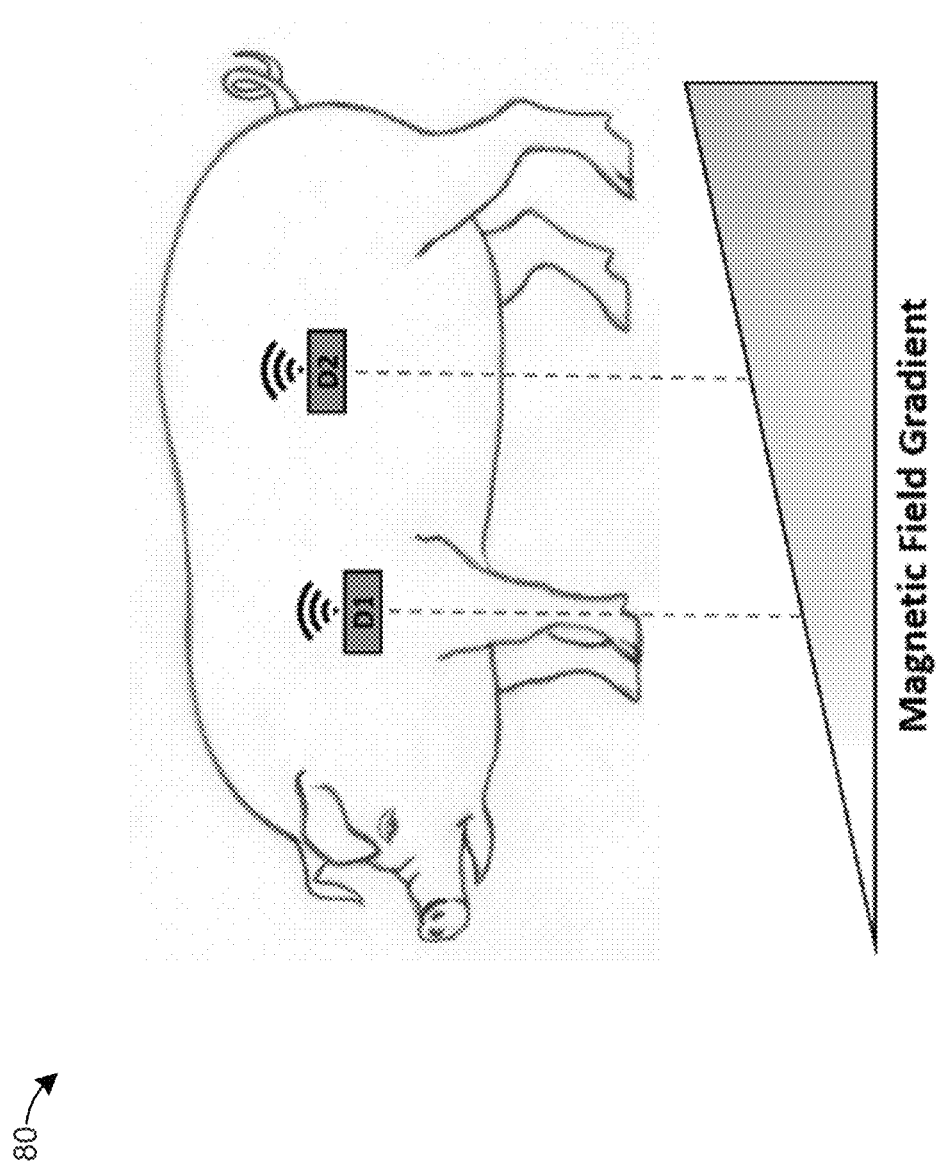
FIG. 8 illustrates an example of a mammal having first and second ingestible magnetic sensors.

FIG. 8 illustrates an example of a mammal 80 having first and second ingestible magnetic sensors D1, D2 in the FOV a three-dimensional magnetic field generator. The first ingestible magnetic sensor D1 is fixed on the outer body of the mammal 80 to serve as reference. The second ingestible magnetic sensor is in the GI tract of the mammal 80 after being ingested. Using apparatus 70, a measurement is taken by each ingestible magnetic sensors D1, D2 when the mammal 80 is in the FOV of the three-dimensional magnetic field generator 100 in the chute 730, as discussed above. Each measurement includes a three-dimensional magnetic field value and a time stamp. The measurements can be sent in real time or later to a receiver that can process them to generate a spatiotemporal map of the trajectory of the ingestible magnetic sensor D2 through the GI tract of the mammal 80.

Figure 9:
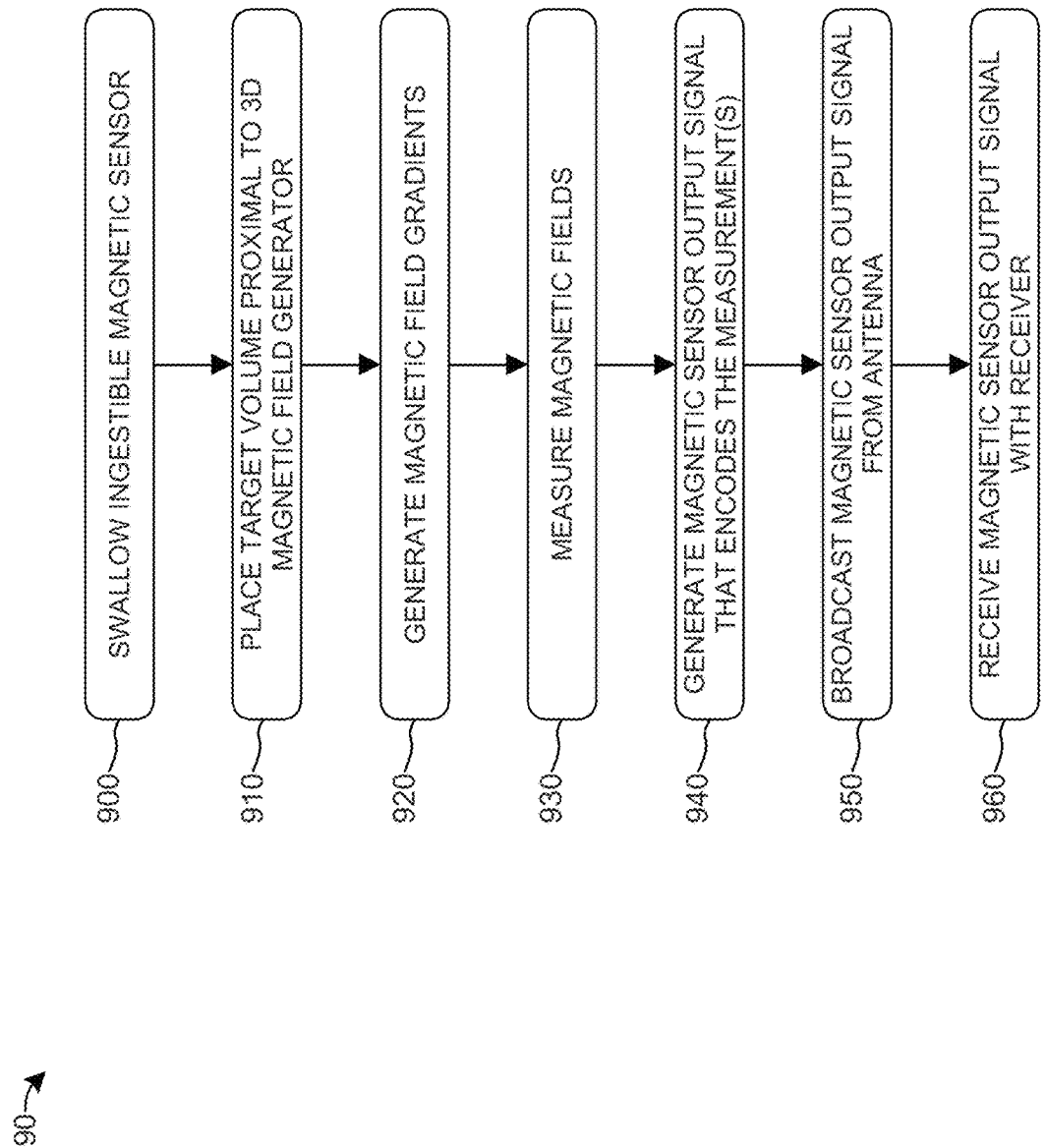
FIG. 9 is a flow chart of a method for in-vivo monitoring of an internal volume of a mammal.

FIG. 9 is a flow chart of a method 90 for in-vivo monitoring of an internal volume of a mammal according to an embodiment. In step 900, the mammal swallows or ingests an ingestible magnetic sensor (e.g., ingestible magnetic sensor 110). Alternatively, the ingestible magnetic sensor can be inserted into a body cavity or surgically placed in the mammal. In step 910, the target internal volume (e.g., the GI tract when mammal swallows or ingests the ingestible magnetic sensor) of the mammal is placed proximal to a three-dimensional magnetic field generator, such as within the FOV of the three-dimensional magnetic field generator.

In step 920, the three-dimensional magnetic field generator generates a plurality of magnetic field gradients. The magnetic field gradients includes a first magnetic field gradient along a first axis (e.g., the X axis), a second magnetic field gradient along a second axis (e.g., the Y axis) that is orthogonal to the first axis, and a third magnetic field gradient along a third axis (e.g., the Z axis) that is orthogonal to the first and second axes. At least a portion and/or a substantial portion of each magnetic field gradient has a monotonically-varying magnitude. The magnetic field gradients can be time-sequenced to encode each magnetic field gradient (e.g., as discussed above with respect to FIG. 2). In some embodiments, the third magnetic field gradient is produced while the first and second magnetic fields are produced. In some embodiments, the first and second magnetic field gradient are not produced or in the "on" state simultaneously.

In some embodiments, the three-dimensional magnetic field generator or the controller for the three-dimensional magnetic field generator sends a signal to the receiver to coordinate or synchronize the timing of the magnetic field gradients. The receiver can relay and/or send another signal to the three-dimensional magnetic sensor in the ingestible magnetic sensor to coordinate or synchronize the timing of the magnetic field gradient measurements.

In step 930, a three-dimensional magnetic sensor in the ingestible magnetic sensor measures the magnetic field gradients at the location of the ingestible magnetic sensor. The three-dimensional magnetic sensor can measure each magnetic field gradient at a different time. For example, three-dimensional magnetic sensor can measure the first magnetic field gradient at a first time, the second magnetic field gradient at a second time, and the third magnetic field at a third time. The magnetic field gradient measurements can be made according to a predetermined time sequence, for example as discussed above with respect to FIG. 2. For example, the first magnetic field gradient can be measured at a first time (or over a first time window) while the both the first and third magnetic field gradients are applied but while the second magnetic field gradient is not applied. The second magnetic field gradient can be measured at a second time (or over a second time window) while the both the second and third magnetic field gradients are applied but while the first magnetic field gradient is not applied. The third magnetic field gradient can be measured at a third time (or over a third time window) while the first and second magnetic field gradients are not applied. The first magnetic field gradient can correspond to a gradient the "X" direction or axis, the second magnetic field gradient can correspond to a gradient along the "Y" direction or axis, and the third magnetic field gradient can correspond to a gradient along the "Z" direction or axis.

The controller can turn on the first and third magnetic field gradients simultaneously while the second magnetic field gradient is in the off state. When the first and third magnetic field gradients have ramped up and are in a stable "on" state, the first time window can begin to measure the first magnetic field gradient. In some embodiments, multiple measurements (e.g., 25 or more) can be taken, from which the average or median can be taken. After the first magnetic field gradient is measured (e.g., in the first time window), the controller can simultaneously turn off the first magnetic field gradient and turn on the second magnetic field gradient while maintaining the third magnetic field gradient in the "on" state. When the second magnetic field gradient has ramped up and is in a stable "on" state and the first magnetic field gradient has ramped down and is in the "off" state, the second time window can begin to measure the second magnetic field gradient. In some embodiments, multiple measurements (e.g., 25 or more) can be taken, from which the average or median can be taken. After the second magnetic field gradient is measured (e.g., in the second time window), the controller can turn off the second magnetic field gradient while maintaining the third magnetic field gradient in the "on" state. When the second magnetic field gradient has ramped down and is in the "off" state, the third time window can begin to measure the third magnetic field gradient. In some embodiments, multiple measurements (e.g., 25 or more) can be taken, from which the average or median can be taken.

The sequence of the ramping up and down and measuring the first and second magnetic field gradients can be reversed. That is, initially the second and third magnetic field gradients can be ramped up to measure the second magnetic field gradient (e.g., in the second time window) while the first magnetic field gradient is off. Then, the second magnetic field gradient can be ramped down at the same time (e.g., simultaneously) that the first magnetic field gradient is ramped up (while maintaining the third magnetic field gradient). Next, the first magnetic field gradient can be measured (e.g., in first time window) while the second magnetic field gradient is off (and the third magnetic field gradient is on). Finally, the first magnetic field gradient is ramped down and then third magnetic field gradient can be measured (e.g., in the third time window).

In an alternative embodiment, the third magnetic field gradient is only turned on to measure the third magnetic field gradient. In this embodiment, the third magnetic field gradient is not in the on state while the first and second magnetic field gradients are measured.

In some embodiments, the three-dimensional magnetic sensor takes the magnetic field measurements in response to one or more control signals sent from the receiver.

In step 940, the three-dimensional magnetic sensor sends the magnetic field measurements to a controller, in the ingestible magnetic sensor, that generates a magnetic sensor output signal that encodes the magnetic field measurements (e.g., the measurement of the first, second, and third magnetic field gradients) and the time that the measurement occurred. In step 950, the magnetic sensor output signal is broadcast from an antenna that is electrically coupled to the microprocessor. The antenna is disposed in the ingestible magnetic sensor.

The controller can generate the magnetic sensor output signal immediately such that the magnetic field measurements are broadcast in real time or substantially real time. Alternatively, the controller can temporarily store one or more magnetic field measurements and can generate one or more magnetic sensor output signals for broadcast by the antenna at a later time.

In step 950, the magnetic sensor output signal is received wirelessly by an external receiver. The external receiver can extract the magnetic field measurement data (e.g., the three-dimensional magnetic field measurements and the time stamp) from the magnetic sensor output signal and store the magnetic field measurement data in a memory accessible by the receiver. In some embodiments, the external receiver can determine the relative three-dimensional position of the ingestible magnetic sensor, with respect to the three-dimensional magnetic field generator, using the magnetic field measurement data. For example, the three-dimensional position can be determined using a look-up table of known magnetic fields and positions (for example produced using apparatus 50) which can be interpolated in some embodiments. In another embodiment, the three-dimensional position can be determined using a model of three-dimensional magnetic field versus relative position. In another embodiment, the three-dimensional position can be determined using machine learning or artificial intelligence based on existing magnetic field measurement data and known positions.

Figure 10:
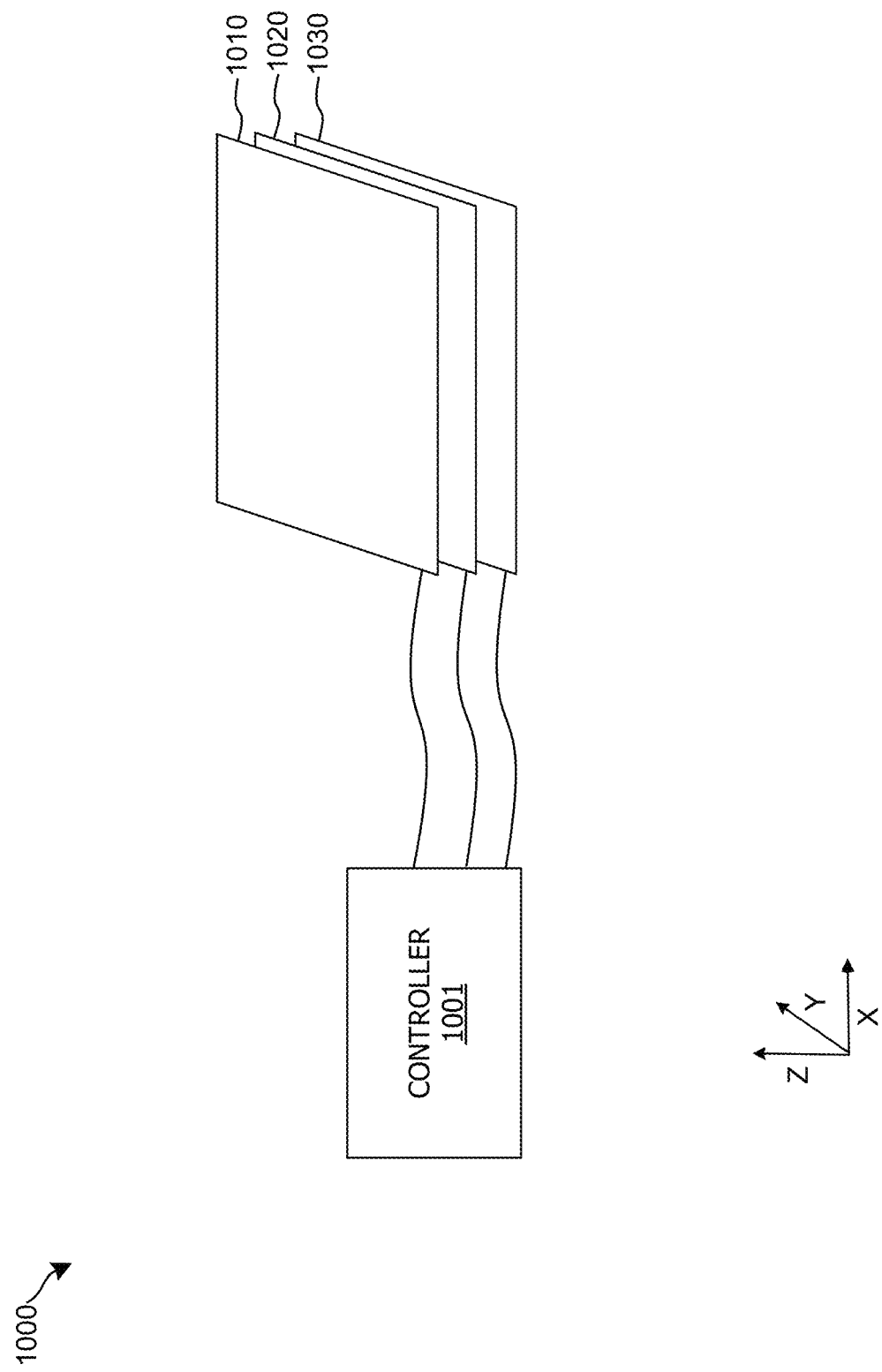
FIG. 10 is a block diagram of an apparatus for producing magnetic field gradients according to an embodiment.

FIG. 10 is a block diagram of an apparatus 1000 for producing magnetic field gradients according to an embodiment. The apparatus 1000 includes a controller 1000, a first electromagnet coil set 1010, a second electromagnet coil set 1020, and a third electromagnet coil set 1030. The first electromagnet coil set 1010 is configured to produce a first magnetic field gradient with respect to a first axis (e.g., the X axis in the Cartesian coordinate system). The second electromagnet coil set 1020 is configured to produce a second magnetic field gradient with respect to a second axis (e.g., the Y axis in the Cartesian coordinate system) that is orthogonal to the first axis. The third electromagnet coil set 1030 is configured to produce a third magnetic field gradient with respect to a third axis (e.g., the Z axis in the Cartesian coordinate system) that is orthogonal to the first and second axes.

The electromagnet coil sets 1010, 1020, 1030 can be stacked together and/or vertically arranged (e.g., in a vertical arrangement with respect to an underlying surface) along the third axis. The electromagnet coil sets 1010, 1020, 1030 are preferably centered (e.g., concentrically centered) and/or aligned, with respect to the first and second axes, with respect to each other. In addition, the electromagnet coil sets 1010, 1020, 1030 each have upper and lower planar surfaces (e.g., orthogonal to the Z axis), which allows them to be stacked and integrated or embedded into a flat device, such as a board, a wall, the back of a chair, a conformable wearable belt, or other location to minimize patient discomfort.

The controller 1000 is electrically coupled to the first electromagnet coil set 1010, the second electromagnet coil set 1020, and the third electromagnet coil set 1030. The controller 1000 is configured to selectively provide power to the first electromagnet coil set 1010, the second electromagnet coil set 1020, and/or the third electromagnet coil set 1030. Selectively powering the electromagnet coil sets 1010, 1020, and/or 1030 can sequentially produce a total magnetic field gradient, with respect to each axis, where at least a portion and/or a substantial portion of each total magnetic field gradient has a monotonically-varying magnitude along the respective axis. For example, the electromagnet coil sets 1010, 1020, and/or 1030 can be selectively powered such that at least a portion of the total magnetic field gradient with respect to the first axis has a monotonically-varying magnitude. In another example, the electromagnet coil sets 1010, 1020, and/or 1030 can be selectively powered such that at least a portion of the total magnetic field gradient with respect to the second axis has a monotonically-varying magnitude. In yet another example, the electromagnet coil sets 1010, 1020, and/or 1030 can be selectively powered such that at least a portion of the total magnetic field gradient with respect to the third axis has a monotonically-varying magnitude. The relative position of a magnetic sensor device, with respect to the electromagnet coil sets 1010, 1020, and/or 1030, can be determined by measuring the total magnetic field while each localization magnetic field gradients is produced. The portion of the total magnetic field gradient with respect to a given axis can be referred to as a field of view (FOV).

Figure 11B:
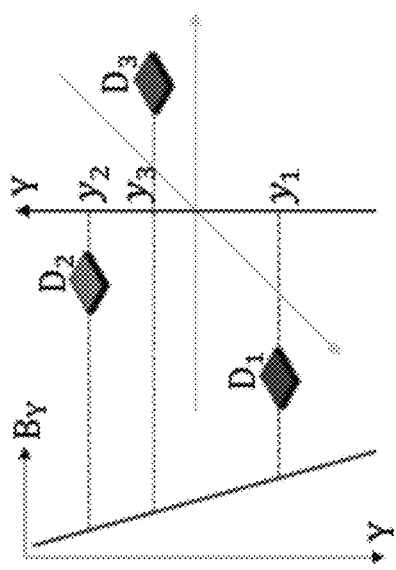
FIGS. 11A, 11B, and 11C are simplified views of the total magnetic field gradients used for encoding the device location.
Figure 11C:
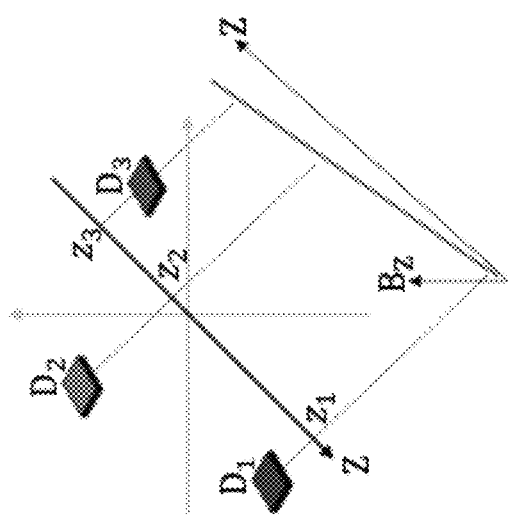
Figure 11A:
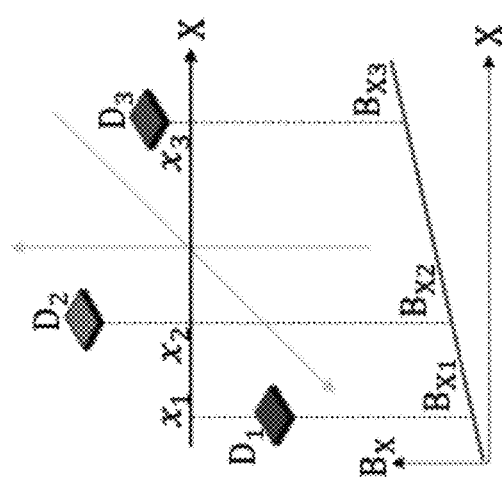

FIGS. 11A-C are simplified views of the total magnetic field gradients used for encoding the device location. Three example magnetic sensor devices $D_1$, $D_2$, and $D_3$ are located in the FOV. To localize the devices $D_1$, $D_2$, and $D_3$ along the X-axis (e.g., the first axis), a magnetic field $B_X$ having a monotonically-varying magnitude is generated with respect to the X-axis, as illustrated in FIG. 11A. The monotonically-varying magnitude has a gradient in the absolute value of the total magnetic field along the X-axis. The gradient ensures that no two points along the X-axis within the FOV have the same absolute total magnetic field value. For example, the magnitude of the total magnetic field $B_X$ measured by devices $D_1$, $D_2$, and $D_3$ can be described according to Equation 1:

$$\|B_{X1}\| < \|B_{X2}\| < \|B_{X3}\| \tag{1}$$

The total magnetic field $B_X$ at each device's X location can be described with respect to the X magnetic field contribution from each orthogonal magnetic field at the corresponding X location, as described in Equation 2. The magnetic field gradient with respect to the X axis can be described according to Equation 3.

$$\|B_{Xi,\ i=1,2,3}\| = \sqrt{B_{Xi\text{-}x}^2 + B_{Xi\text{-}y}^2 + B_{Xi\text{-}z}^2} \tag{2}$$

$$X\ \text{Gradient} = G_X = \partial B_X / \partial X \tag{3}$$

Similarly, to localize the devices $D_1$, $D_2$, and $D_3$ along the Y-axis (e.g., the second axis), a magnetic field By having a monotonically-varying magnitude is generated with respect to the Y-axis, as illustrated in FIG. 11B. The monotonically-varying magnitude has a gradient in the absolute value of the total magnetic field along the Y-axis. The gradient ensures that no two points along the Y-axis within the FOV have the same absolute total magnetic field value. For example, the magnitude of the total magnetic field By measured by devices $D_1$, $D_2$, and $D_3$ can be described according to Equation 4:

$$\|B_{Y2}\| < \|B_{Y3}\| < \|B_{Y1}\| \tag{4}$$

The total magnetic field By at each device's Y location can be described with respect to the Y magnetic field contribution from each orthogonal magnetic field at the corresponding Y location, as described in Equation 5. The magnetic field gradient with respect to the Y axis can be described according to Equation 6.

$$\|B_{Yi,\ i=1,2,3}\| = \sqrt{B_{Yi\text{-}x}^2 + B_{Yi\text{-}y}^2 + B_{Yi\text{-}z}^2} \tag{5}$$

$$Y\ \text{Gradient} = G_Y = \partial B_Y / \partial Y \tag{6}$$

Likewise, to localize the devices $D_1$, $D_2$, and $D_3$ along the Z-axis (e.g., the third axis), a magnetic field $B_Z$ having a monotonically-varying magnitude is generated with respect to the Z-axis, as illustrated in FIG. 11C. The monotonically-varying magnitude has a gradient in the absolute value of the total magnetic field along the Z-axis. The gradient ensures that no two points along the Z-axis within the FOV have the same absolute total magnetic field value. For example, the magnitude of the total magnetic field $B_Z$ measured by devices $D_1$, $D_2$, and $D_3$ can be described according to Equation 7:

$$\|B_{Z1}\| < \|B_{Z2}\| < \|B_{Z3}\| \tag{7}$$

The total magnetic field $B_Z$ at each device's Z location can be described with respect to the Z magnetic field contribution from each orthogonal magnetic field at the corresponding Z location, as described in Equation 8. The magnetic field gradient with respect to the Y axis can be described according to Equation 9.

$$\|B_{Zi,\ i=1,2,3}\| = \sqrt{B_{Zi\text{-}x}^2 + B_{Zi\text{-}y}^2 + B_{Zi\text{-}z}^2} \tag{8}$$

$$Z\ \text{Gradient} = G_Z = \partial B_Z / \partial Z \tag{9}$$

Using these magnetic field measurements along three orthogonal axes, the complete 3D position of each device $D_1$, $D_2$, and $D_3$ can be decoded unambiguously. Since the gradient manifests in the total and absolute magnetic field values along any axis, this localization technique is immune to potential inaccuracies caused by device mis-alignment and orientation mis-match relative to any specific coordinate. As the device orientation changes, the individual field components in Equations 2, 5, and 8 may change but the overall magnitude remains the same.

In order to generate the required spatial gradients in the magnetic field along the three axes, electromagnetic coils (e.g., electromagnet coil sets 1010, 1020, and/or 1030) can be designed with one or more of the following design goals: (i) high gradient strength G to achieve high resolution; (ii) planar or substantially planar coils that can be placed close to the patient, such as beneath or in the patient's bed; (iii) enhanced FOV to allow sufficient room for medical procedure navigation, observation, and/or alignment; (iv) high current efficiency to make the maximum use of current drawn by the gradient coils; and/or (v) low coil-length to have less inductance (for fast switching) and less resistance (for lower heating). The gradient coil efficiency η is defined as the ratio of the magnetic field gradient (G) produced by the coil to the current drawn (I). The geometrical design of the coils and static magnetic field simulations can be carried out in a magneto-static software such as Radia, available from the European Synchrotron Radiation Facility. The FOV can be 15 cm×15 cm×10 cm (X×Y×Z) though other FOVs can be provided.

The spatial localization resolution (ax) obtained by the system is given by Equation 10:

$$\Delta x = \Delta B_{eff}/G \quad (10)$$

where $\Delta B_{eff}$ is the effective resolution that the magnetic sensor can achieve while performing a magnetic field measurement. It is dictated by the noise of the sensing and processing units, most dominant being the quantization noise. G is the applied magnetic field gradient, which is determined by the current in electromagnets and their geometrical structure. There are two predominant noise sources that can cause G to vary from the required ideal value: (a) the offset due to variations in supply current, denoted by $\delta G_s$, and (b) the interpolation error caused during gradient characterization, denoted by $\delta G_i$. To get $\Delta x < 100$ μm with G=30 mT/m, it is required to have $\Delta B_{eff} < 3$ μT. To keep G consistently at 30 mT/m, $\delta G_s + \delta G_i$ are targeted to be <1%. In other embodiments, a lower resolution can be provided (e.g., $\Delta x < 500$ μm).

Figure 12:
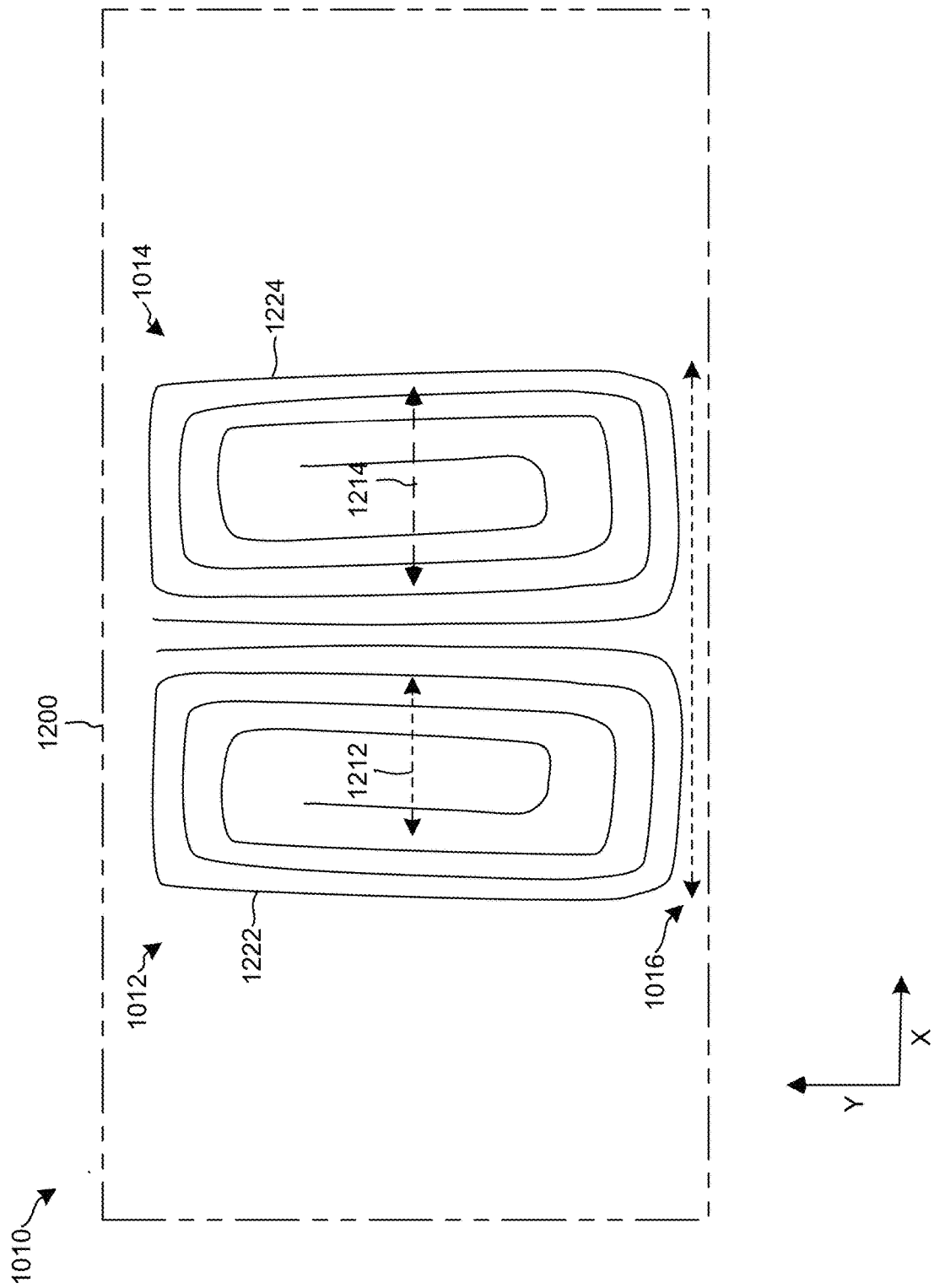
FIG. 12 is a schematic top view of the first electromagnet coil set according to an embodiment.

FIG. 12 is a schematic top view of the first electromagnet coil set 1010 according to an embodiment. The first electromagnet coil set 1010 includes a clockwise spiral winding 1012 and a counterclockwise spiral winding 1014 that are disposed adjacent to or next to each other. The spiral windings 1012, 1014 can be mirror images of each other. Each spiral winding 1012, 1014 has an axis of symmetry 1212, 1214 that is parallel to the first axis (e.g., the X axis). The axes of symmetry 1212, 1214 are aligned in the spiral windings 1012, 1014 to produce a uniform or substantially uniform magnetic field gradient (e.g., a first magnetic field gradient) with respect to the first axis. The spiral windings 1012, 1014 are elongated along the second axis (e.g., the Y axis), such as to form ovals, racetracks (e.g., stadium shapes), rectangles, rounded rectangles, or other elongated shapes. The spiral windings 1012, 1014 can have an elongated length of about 15 cm along the second Y axis which can keep the X-gradient substantially homogenous across the Y FOV. The width 1016 of the first electromagnet coil set 1010 is measured along or parallel to the first axis (e.g., the X axis). The width 1016 of the first electromagnet coil set 1010

The spiral windings 1012, 1014 are formed by respective wires 1222, 1224 (e.g., first and second wires). Alternatively, more than one wire can be connected together to form a spiral winding. The spiral windings 1012, 1014 have a thickness (e.g., a profile) defined by the thickness of the respective wires 1222, 1224. The wires 1222, 1224 can be identical and thus have the same thickness. Thus, the spiral windings 1222, 1224 have top and bottom planar surfaces (or substantially planar surfaces (e.g., at least 95% planar)) that are parallel to X-Y plane 1200. The top and bottom planar surfaces of the spiral windings 1222, 1224 are defined by the respective top and bottom surfaces of wires 1222, 1224. The thickness of the spiral windings 1222, 1224 with respect to the third axis (e.g., the Z axis) is equal to the thickness of the wires 1222, 1224. The wires 1222, 1224 can have an appropriate number of windings or turns to produce the first magnetic field gradient.

The wires 1222, 1224 can be configured to receive a DC current in the range of about 10 A to about 50 A, including about 20 A, about 30 A, and about 40 A, or another current. For example, the wires 1222, 1224 can be copper wires such as Litz 50/32 AWG wires, which denotes 50 strands of 32 AWG wires bundled together. The wires 1222, 1224 have an insulated covering to prevent electrical shorting therebetween.

Figure 13:
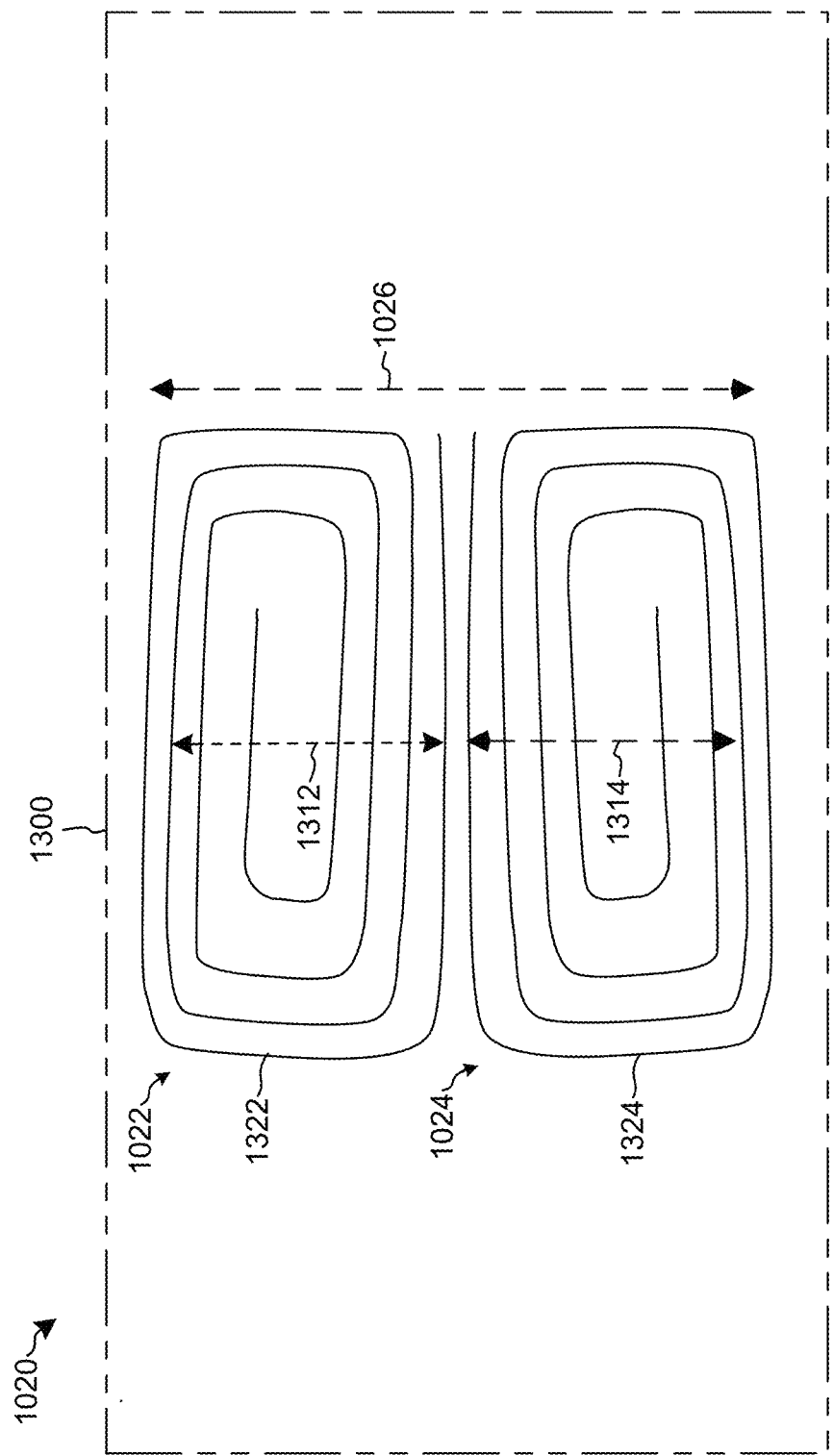
FIG. 13 is a schematic top view of the second electromagnet coil set according to an embodiment.

FIG. 13 is a schematic top view of the second electromagnet coil set 1020 according to an embodiment. The second electromagnet coil set 1020 includes a clockwise spiral winding 1022 and a counterclockwise spiral winding 1024 that are disposed adjacent to or next to each other. The spiral windings 1022, 1024 can be mirror images of each other. Each spiral winding 1022, 1024 has an axis of symmetry 1312, 1314 that is parallel to the second axis (e.g., the Y axis). The axes of symmetry 1312, 1314 are aligned in the spiral windings 1022, 1024 to produce a uniform or substantially uniform magnetic field gradient (e.g., a second magnetic field gradient) with respect to the second axis. The second electromagnet coil set 1020 is the same as the first electromagnet coil set 1010 except that the second electromagnet coil set 1020 is rotated by 90 degrees compared to the first electromagnet coil set 1010. In other embodiments, the second electromagnet coil set 1020 can have other configuration differences compared to the first electromagnetic coil set 1010.

The spiral windings 1022, 1024 are formed by respective wires 1322, 1324 (e.g., third and fourth wires). Alternatively, more than one wire can be connected together to form a spiral winding. The spiral windings 1022, 1024 have a thickness (e.g., a profile) defined by the thickness of the respective wires 1322, 1324. The wires 1322, 1324 can be identical and thus have the same thickness. Thus, the spiral windings 1022, 1024 have top and bottom planar surfaces (or substantially planar surfaces (e.g., at least 95% planar)) that are parallel to X-Y plane 1300. The top and bottom planar surfaces of the spiral windings 1022, 1024 are defined by the respective top and bottom surfaces of wires 1322, 1324. The thickness of the spiral windings 1022, 1024 with respect to the third axis (e.g., the Z axis) is equal to the thickness of the wires 1322, 1324. The wires 1322, 1324 can have an appropriate number of windings or turns to produce the second magnetic field gradient. The length 1026 of the second electromagnet coil set 1020 is measured along or parallel to the second axis (e.g., the Y axis).

The wires 1322, 1324 can be configured to receive a DC current in the range of about 10 A to about 50 A, including about 20 A, about 30 A, and about 40 A, or another current. For example, the wires 1322, 1324 can be Litz 50/32 AWG wires. The wires 1322, 1324 can be the same as or different than the respective wires 1222, 1224.

Figure 14:
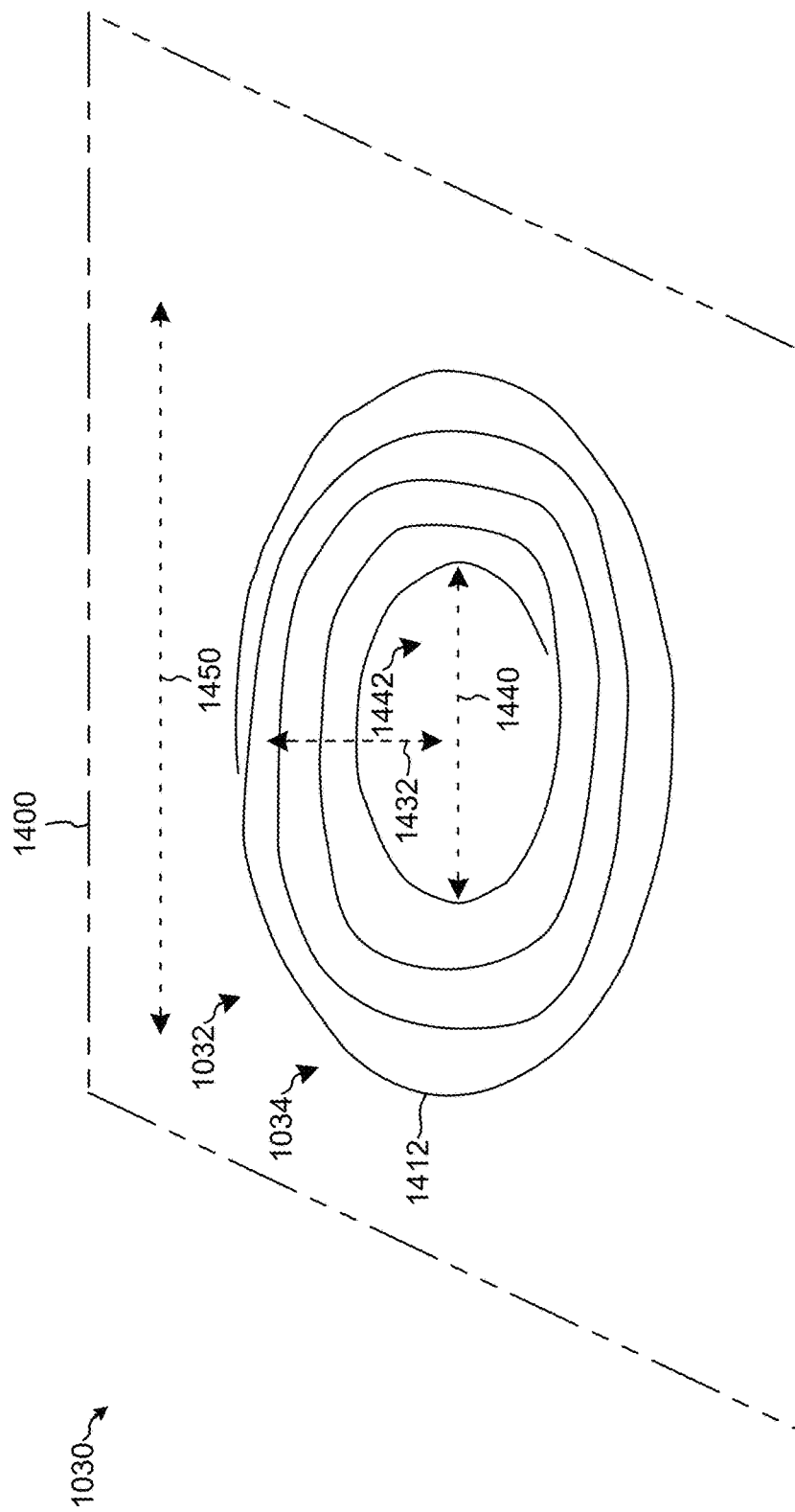
FIG. 14 is a schematic perspective view of the third electromagnet coil set according to an embodiment.

FIG. 14 is a schematic perspective view of the third electromagnet coil set 1030 according to an embodiment. The third electromagnet coil set 130 includes a spiral winding 1032 that includes one or more wires 1412 that is/are wound in the shape of an annulus, disc, or ring 1034 (in general, annulus). In an embodiment, two or more wires 612 are wound next to each other to form the annulus 1034. The wire(s) 1412 are wound in a counter-clockwise direction but in other embodiments the wire(s) 1412 can be wound in a clockwise direction.

The annulus 134 has an inner diameter 1440 and an outer diameter 1450, where the inner diameter 1450 defines a hollow region or inner cavity 1442 that does not include the wire(s) 1412. The ratio of the outer diameter 1450 to the inner diameter 1440 can be selected to allow an appropriate number of windings or turns of the wire(s) 1412, to produce the third magnetic field gradient. In a specific embodiment, the outer diameter 1450 can be about 28 cm and the inner diameter 1440 can be about 10 cm. The wire(s) 1412 can have an insulated covering to prevent electrical shorting therebetween.

The spiral winding 1032 has an axis of symmetry 1432 that is parallel to the third axis (e.g., the Z axis). The spiral winding 1032 has a thickness (e.g., a profile) defined by the thickness of the wire(s) 1412. Thus, the spiral winding 1032 has top and bottom planar surfaces (or substantially planar surfaces (e.g., at least 95% planar)) that are parallel to X-Y plane 1400. The top and bottom planar surfaces of the spiral winding 1032 are defined by the respective top and bottom surfaces of wire(s) 1412. The thickness of the spiral winding 1032 with respect to the third axis (e.g., the Z axis) is equal to the thickness of the wire(s) 1412. The wire(s) 1412 can have an appropriate number of windings or turns to produce the third magnetic field gradient.

The wire(s) 1412 can be configured to receive a DC current in the range of about 10 A to about 50 A, including about 20 A, about 30 A, and about 40 A, or another current. For example, the wires wire(s) 1412 can be Litz 50/32 AWG wires. The wire(s) 1412 can be the same as or different than wires 1222, 1224, 1322, and/or 1324.

Figure 15:
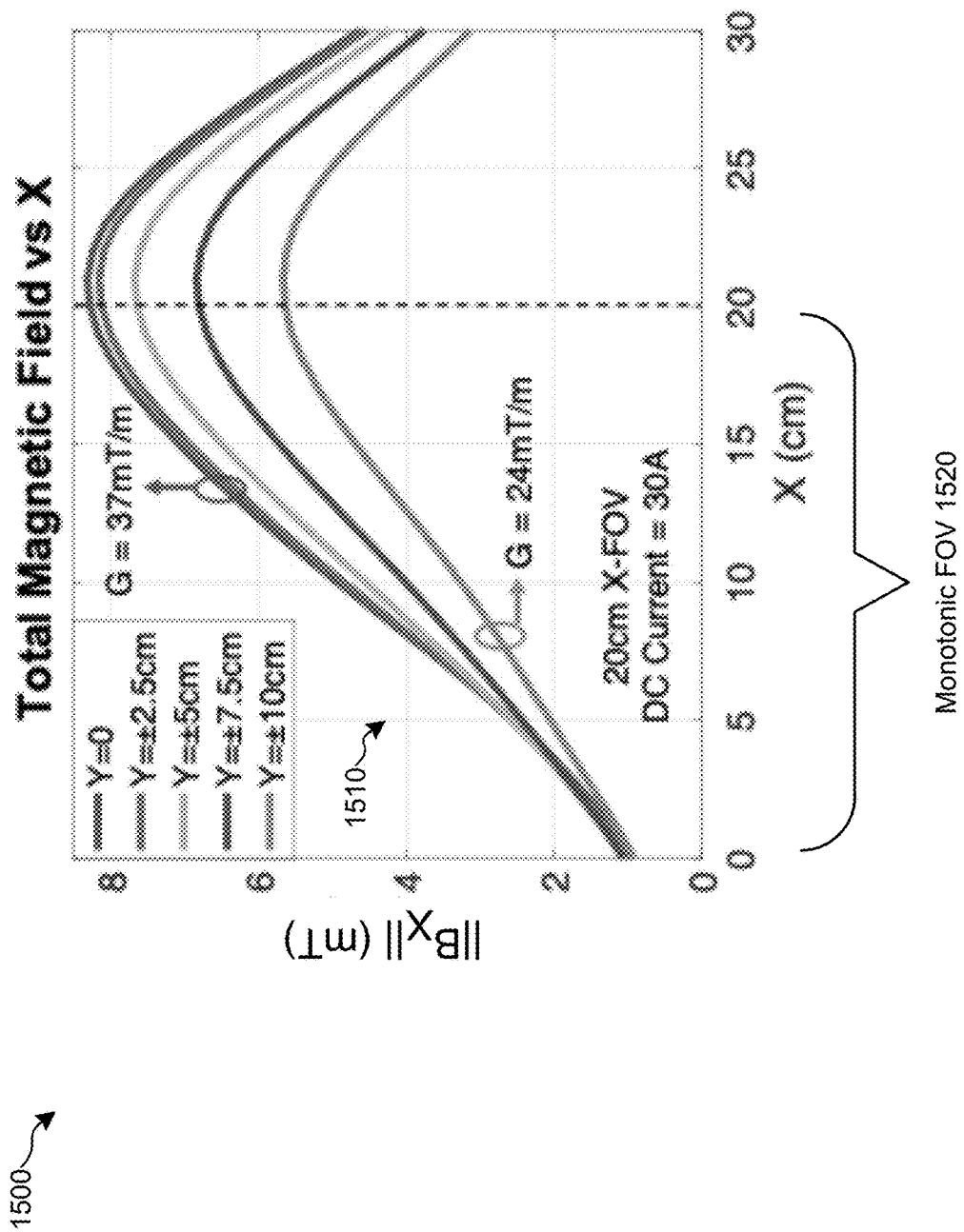
FIG. 15 is a graph that illustrates an example of the total magnetic fields ($\|B_X\|$) produced simultaneously by the first and third electromagnet coil sets.

FIG. 15 is a graph 1500 that illustrates an example of the total magnetic field gradients 1510 ($\|B_X\|$) produced simultaneously by the first and third electromagnet coil sets 1010, 1030. The graph 1500 illustrates the total magnetic fields 1510 (e.g., first localization magnetic field gradients) for different Y values from 0 to ±10 cm at ±2.5 cm intervals, while keeping Z=7.5 cm, at various X values. Due to the non-homogenous nature of the Z-coil's magnetic field along the X-axis as the Y-coordinate is varied, the total magnetic field gradient strength reduces monotonically from 37 mT/m at Y=0 to 24 mT/m at Y=+10 cm. A DC current of 30 A was used in the first and third electromagnet coil sets 1010, 1030 to produce the total magnetic fields 1510. When operated simultaneously at 30 A of DC power, the first and third electromagnet coil sets 1010, 1300 have a monotonic X FOV 1520 of about 20 cm in which the magnitude of the total magnetic field 1510 varies (increases) monotonically.

Thus, the ratio of the 20 cm X FOV 1520 to the width 1016 of the first magnetic coil set 1010 (30 cm when producing the total magnetic field gradients 1510) is about 2:3, though the ratio can range from 1:2 to about 3:4 in other embodiments (e.g., less than or equal and/or greater than or equal to 2:3).

Figure 16:
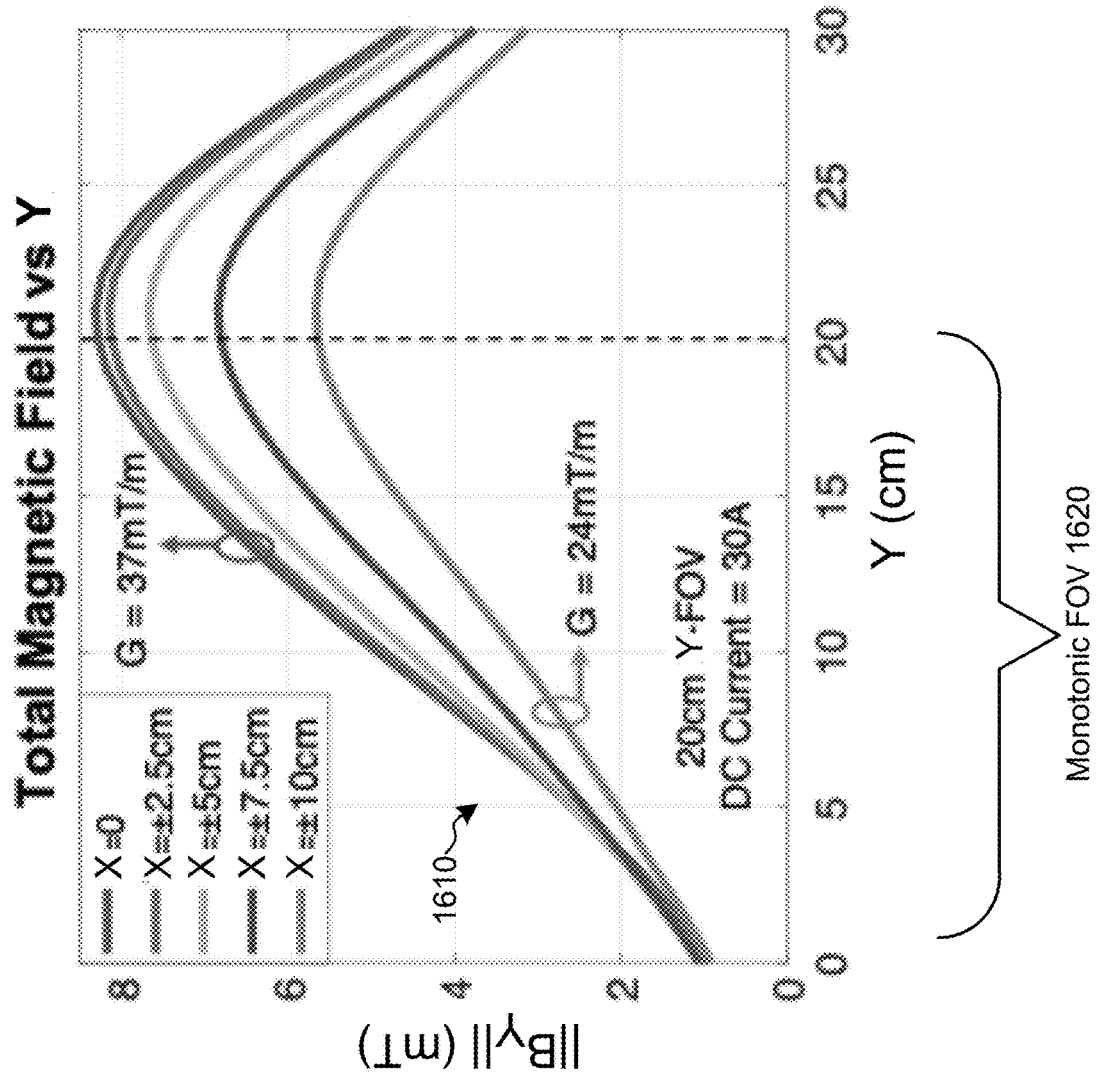
FIG. 16 is a graph that illustrates an example of the total magnetic fields produced simultaneously by the second and third electromagnet coil sets.

FIG. 16 is a graph 1600 that illustrates an example of the total magnetic field gradients 1610 produced simultaneously by the second and third electromagnet coil sets 1020, 1030. The graph 1600 illustrates the total magnetic field gradients 1610 (e.g., second localization magnetic field gradients) for different X values from 0 to ±10 cm at ±2.5 cm intervals, while keeping Z=7.5 cm, at various Y values. Due to the non-homogenous nature of the Z-coil's magnetic field along the Y-axis as the X-coordinate is varied, the total gradient strength reduces monotonically from 37 mT/m at X=0 to 24 mT/m at X=±10 cm, similar to graph 1500. A DC current of 30 A was used in the second and third electromagnet coil sets 1020, 1030 to produce the total magnetic fields 1610. When operated simultaneously at 30A of DC power, the second and third electromagnet coil sets 1020, 1030 have a monotonic Y FOV 1620 of about 20 cm in which the magnitude of the total magnetic field 1610 varies (increases) monotonically.

Thus, the ratio of the 20 cm Y FOV 1620 to the length 126 of the second magnetic coil set 110 (30 cm when producing the total magnetic field gradients 1610) is about 2:3, though the ratio can range from 1:2 to about 3:4 in other embodiments (e.g., less than or equal and/or greater than or equal to 2:3).

Figure 17:
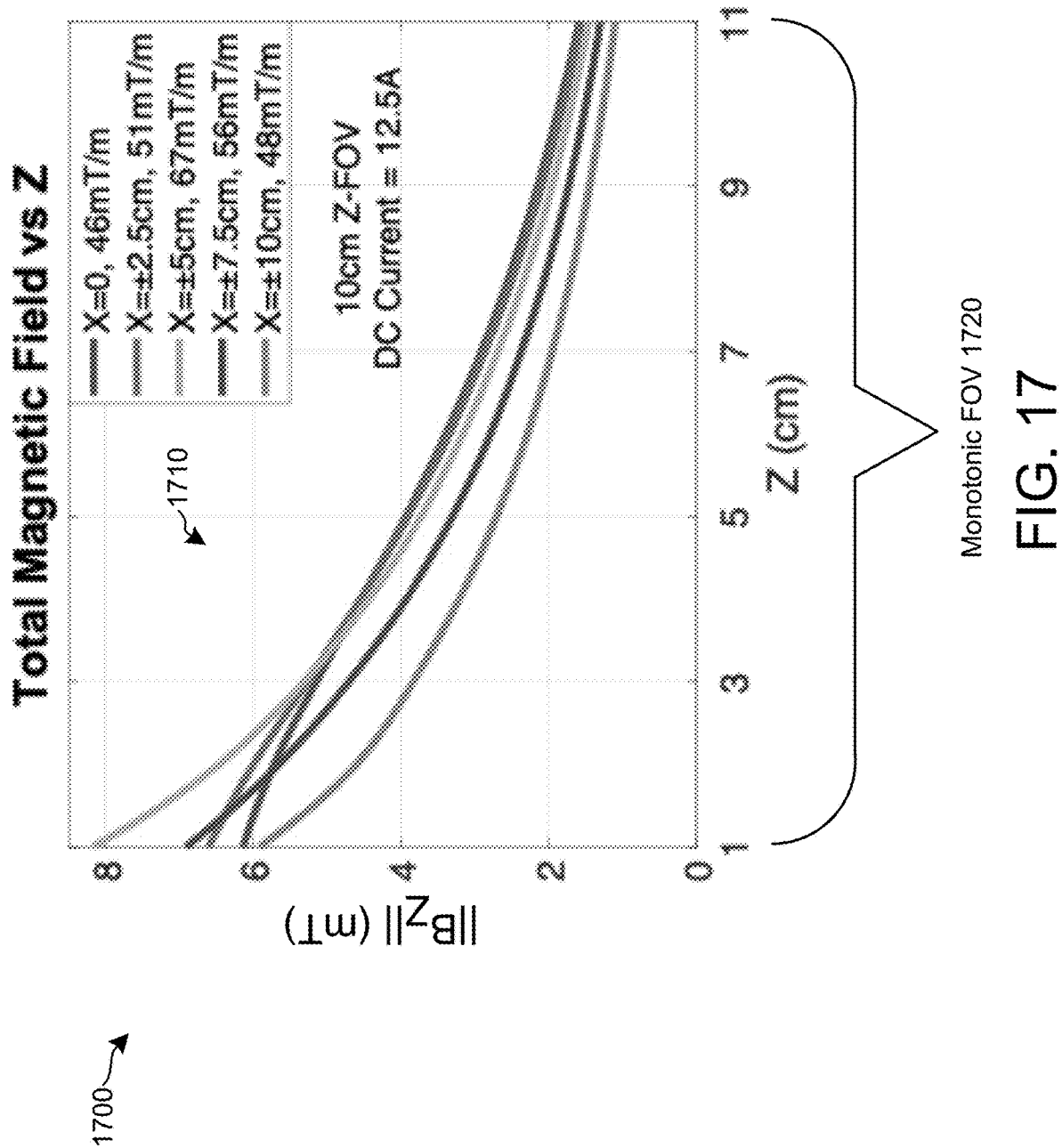
FIG. 17 is a graph that illustrates an example of the monotonically-varying magnetic total fields ($\|B_Z\|$) produced by the third electromagnet coil set.

FIG. 17 is a graph 1700 that illustrates an example of the monotonically-varying magnetic total fields 1710 ($\|B_Z\|$) produced by the third electromagnet coil set 1030. Each total magnetic field 1710 (e.g., third localization magnetic field) plot was measured a respective relative X position as a function of Z position. Each total magnetic field 1710 plot was measured using a relative Y position of 0 cm. In addition, each total magnetic field 1710 was measured over 10 cm from Z=1 cm to Z=11 cm, where the Z distance is the height from the top surface of the third electromagnet coil set 1030.

In general, the magnitude of the total magnetic fields 1710 decreases monotonically and with increasing height (Z position) from the third electromagnet coil set 1030. In addition, the total magnetic fields 1710 are linear over most heights (Z). It is believed that the inner cavity 1442 enhances the linearity of the total magnetic fields 1710, which is more exponential in the absence of the inner cavity 1442. The third electromagnet coil set 1030 has a monotonic Z FOV 1720 of about 10 cm in which the magnitude of the total magnetic field 1710 varies (decreases) monotonically.

Thus, the ratio of the 10 cm Z FOV 1720 to the outer diameter 1450 (30 cm when producing the total magnetic field gradients 1710) of the third magnetic coil set 1030 is about 1:3, though the ratio can range from 1:4 to about 2:5 in other embodiments (e.g., less than or equal and/or greater than or equal to 1:3). In addition, the ratio of the 10 cm Z FOV 1720 to the inner diameter 1440 (10 cm when producing the total magnetic field gradients 1710) of the third magnetic coil set 1030 is about 1:1, though the ratio can range from about 4:5 to about 6:5 in other embodiments (e.g., less than or equal and/or greater than or equal to 1:1).

The gradient strength G is 46 mT/m at X=0 cm, reaches a maximum of 67 mT/m at X=±5 cm, and comes down to 48 mT/m at X=±10 cm, thus ensuring G>30 mT/m over a length of 20 cm along the X-axis. A DC current of 12.5 A was used in the third electromagnet coil set 1030 to produce the graph 1700, which results in an average magnetic gradient efficiency η of 4.3 mT/m/A.

Since the spiral winding 1032 is symmetrical with respect to the X and Y axes, the total magnetic fields are the same when measured at a relative X position of 0 cm, at relative Y positions of ±2.5 cm, ±5 cm, ±7.5 cm, and ±10 cm, and from Z=1 cm to Z=11 cm (i.e., where X and Y are switched in graph 1700).

The invention should not be considered limited to the particular embodiments described above. Various modifications, equivalent processes, as well as numerous structures to which the present invention may be applicable, will be readily apparent to those skilled in the art to which the present invention is directed upon review of the present disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A method for in-vivo monitoring of a target internal volume of a mammal, comprising:
    placing the target internal volume proximal to a three-dimensional magnetic field generator;
    using the three-dimensional magnetic field generator to sequentially produce:
        a first localization magnetic field gradient along a first axis, a portion of the magnitude of the first localization magnetic field gradient being monotonically-varying along the first axis through the target internal volume and uniquely encoding a position along said first axis corresponding to a strength of said monotonically-varying first localization magnetic field in said target internal volume, the first localization magnetic field gradient produced at a first time;
        a second localization magnetic field gradient along a second axis that is orthogonal to the first axis, a portion of the magnitude of the second localization magnetic field gradient being monotonically-varying along the second axis through the target internal volume and uniquely encoding a position along said second axis corresponding to a strength of said monotonically-varying second localization magnetic field in said target internal volume, the second localization magnetic field gradient produced at a second time that is different than the first time; and
        a third localization magnetic field gradient along a third axis that is orthogonal to the first and second axes, a portion of the magnitude of the third localization magnetic field gradient being monotonically-varying along the third axis through the target internal volume and uniquely encoding a position along said third axis corresponding to a strength of said monotonically-varying third localization magnetic field in said target internal volume, the third localization magnetic field gradient produced at a third time that is different than the first and second times;

measuring a total magnetic field magnitude at the first, second, and third times with a three-dimensional magnetic sensor disposed in an ingestible capsule disposed in the target internal volume;

with a controller disposed in the ingestible capsule and in electrical communication with the three-dimensional magnetic sensor, generating a magnetic sensor output signal that encodes a first total magnetic field magnitude measurement, a second total magnetic field magnitude measurement, and a third total magnetic field magnitude measurement that correspond to the first, second, and third magnetic field gradients, respectively;

broadcasting the magnetic sensor output signal from an antenna disposed in the ingestible capsule, the antenna electrically coupled to the controller; and receiving the magnetic sensor output signal with a receiver;

wherein:
the first localization magnetic field gradient is formed by simultaneously producing:
a first magnetic field with a first planar electromagnet coil set, the first magnetic field having a first-axis magnetic field gradient along the first axis, and
a third magnetic field with a third planar electromagnet coil set, the third magnetic field having a third-axis magnetic field gradient along the third axis, and
the first localization magnetic field gradient comprises a first total magnetic field of the first magnetic field and the third magnetic field.

2. The method of claim 1, further comprising ingesting the ingestible capsule.

3. The method of claim 1, further comprising measuring the total magnetic field magnitude of the first total magnetic field with the three-dimensional magnetic sensor at the first time while only the first and third magnetic fields are simultaneously produced.

4. The method of claim 3, further comprising after measuring the total magnetic field magnitude of the first total magnetic field:
turning off the first magnetic field;
turning on a second magnetic field with a second planar electromagnet coil set, the second magnetic field having a second-axis magnetic field gradient along the second axis; and
simultaneously generating only the second and the third magnetic fields, wherein the second localization magnetic field gradient comprises a second total magnetic field of the second magnetic field and the third magnetic field.

5. The method of claim 4, further comprising measuring the total magnetic field magnitude of the second total magnetic field with the three-dimensional magnetic sensor at the second time while only the second and third magnetic fields are simultaneously produced.

6. The method of claim 5, further comprising after measuring the total magnetic field magnitude of the second total magnetic field:

turning off the second magnetic field while continuing to produce the third magnetic field, wherein the third localization magnetic field gradient comprises a third total magnetic field of the third magnetic field; and measuring the total magnetic field magnitude of the third total magnetic field with the three-dimensional magnetic sensor at the third time while only the third magnetic field is turned on.

7. The method of claim 1, further comprising sending a control signal from the receiver to the controller that causes the three-dimensional magnetic sensor to sequentially measure the total magnetic field magnitude at the first, second, and third times.

8. The method of claim 1, further comprising determining a three-dimensional spatial location of the ingestible capsule based on the total magnetic field magnitude measurements at the first, second, and third times, the spatial location determined relative to the three-dimensional magnetic field generator.

9. The method of claim 8, further comprising using a look-up table to determine the spatial location, the look-up table including a plurality of reference total magnetic field measurements taken at known locations relative to the three-dimensional magnetic field generator.

10. A system for in-vivo monitoring of an internal volume of a mammal, comprising:
a three-dimensional magnetic field generator configured to sequentially produce:
a first localization magnetic field gradient along a first axis, a portion of the magnitude of the first localization magnetic field gradient being monotonically-varying along the first axis through the target internal volume and uniquely encoding a position along said first axis corresponding to a strength of said monotonically-varying first localization magnetic field in said target internal volume,
a second localization magnetic field gradient along a second axis that is orthogonal to the first axis, portion of the magnitude of the second localization magnetic field gradient being monotonically-varying along the second axis through the target internal volume and uniquely encoding a position along said second axis corresponding to a strength of said monotonically-varying second localization magnetic field in said target internal volume, and
a third localization magnetic field gradient along a third axis that is orthogonal to the first and second axes, a portion of the magnitude of the third localization magnetic field gradient being monotonically-varying along the third axis through the target internal volume and uniquely encoding a position along said third axis corresponding to a strength of said monotonically-varying third localization magnetic field in said target internal volume; and
an ingestible magnetic sensor comprising:
a three-dimensional magnetic sensor that outputs measurements of respective magnetic fields corresponding to the first, second, and third localization magnetic field gradients, respectively;
a first controller electrically coupled to the three-dimensional magnetic sensor, the controller generating a magnetic sensor output signal that encodes the measurements of the respective magnetic fields;
an antenna electrically coupled to the first controller, the antenna broadcasting the magnetic sensor output signal;

a power source electrically coupled to the three-dimensional magnetic sensor and the first controller; and
an ingestible capsule having an internal cavity in which the three-dimensional magnetic sensor, the first controller, the antenna, and the power source are disposed, wherein:
the three-dimensional magnetic field generator comprises:
a first planar electromagnet coil set configured to generate a first magnetic field having a first magnetic field gradient along the first axis;
a second planar electromagnet coil set configured to generate a second magnetic field having a second magnetic field gradient along the second axis;
a third planar electromagnet coil set configured to generate a third magnetic field having a third magnetic field gradient along the third axis; and
a second controller configured to selectively provide power to the first electromagnet coil set, the second electromagnet coil set, and/or the third electromagnet coil set to sequentially produce the first, second, and third localization magnetic field gradients,
the second controller selectively provides power to only the first and third planar electromagnet coil sets to simultaneously generate only the first and third magnetic fields, wherein the first localization magnetic field gradient comprises a total magnetic field of the first and third magnetic fields, and
the three-dimensional magnetic sensor measures the respective magnetic field corresponding to the first localization magnetic field gradient while only the first and third magnetic fields are generated.

11. The system of claim 10, further comprising a receiver that receives the magnetic sensor output signal.

12. The system of claim 11, wherein the receiver is configured to determine a three-dimensional spatial location of the ingestible magnetic sensor based on the measurements of the respective magnetic fields, the three-dimensional spatial location determined relative to the three-dimensional magnetic field generator.

13. The system of claim 12, wherein the receiver is configured to display the spatial location on a user interface on or coupled to the receiver.

14. The system of claim 10, wherein:
the second controller selectively provides power to only the second and third planar electromagnet coil sets to simultaneously generate only the second and third magnetic fields, wherein the second localization magnetic field gradient comprises a total magnetic field of the second and third magnetic fields, and
the three-dimensional magnetic sensor measures the respective magnetic field corresponding to the second localization magnetic field gradient while only the second and third magnetic fields are generated.

15. The system of claim 14, wherein:
the second controller selectively provides power to only the third planar electromagnet coil set to generate only the third magnetic field, wherein the third localization magnetic field gradient comprises a total magnetic field of the third magnetic field, and
the three-dimensional magnetic sensor measures the respective magnetic field corresponding to the third localization magnetic field gradient while only the third magnetic field is generated.

16. The system of claim 10, wherein the ingestible magnetic sensor further comprises an antenna-matching circuit electrically coupled to the controller and the antenna.

17. The system of claim 10, wherein the three-dimensional magnetic field generator is disposed on a back of a chair or on a platform.

18. The system of claim 10, wherein:
the first planar electromagnet coil set has a width that is parallel to the first axis, and
a ratio of (a) the at least a portion of the first localization magnetic field gradient that has the monotonically-varying magnetic field magnitude along the first axis to (b) the width of the first electromagnet coil set is within a range of about 1:2 to about 3:4.

19. The system of claim 18, wherein:
the ratio is a first ratio,
the second planar electromagnet coil set has a length that is parallel to the second axis, and
a second ratio of (c) the at least a portion of the second localization magnetic field gradient that has the monotonically-varying magnetic field magnitude along the second axis to (d) the length of the second electromagnet coil set is within a range of about 1:2 to about 3:4.

20. The system of claim 19, wherein:
the third planar electromagnet coil set has a shape of an annulus having an inner diameter and an outer diameter, and
a third ratio of (e) the at least a portion of the third localization magnetic field gradient that has the monotonically-varying magnetic field magnitude along the third axis to (f) the outer diameter of the annulus is within a range of about 1:4 to about 2:5.

* * * * *